(12) United States Patent
Heinlein et al.

(10) Patent No.: US 8,428,324 B2
(45) Date of Patent: Apr. 23, 2013

(54) METHOD AND APPARATUS FOR PROCESSING DIGITAL MAMMOGRAPHIC IMAGES WITH PARALLEL MULTI-SCALE DECOMPOSITION AND RECOMBINING IN AN OPTIMIZED MULTI-SCALE RECONSTRUCTION

(75) Inventors: Peter Heinlein, München (DE); Wilfried Schneider, Wittenbeck (DE); Marco Blumenthal, Jena (DE)

(73) Assignee: General Electric Company, Schenectady, NY (US)

( * ) Notice: Subject to any disclaimer, the term of this patent is extended or adjusted under 35 U.S.C. 154(b) by 964 days.

(21) Appl. No.: 12/276,403

(22) Filed: Nov. 23, 2008

(65) Prior Publication Data
US 2009/0185733 A1 Jul. 23, 2009

(30) Foreign Application Priority Data

Nov. 23, 2007 (DE) .......................... 10 2007 057 013

(51) Int. Cl.
| | | |
|---|---|---|
| *G06K 9/00* | (2006.01) | |
| *G01V 3/00* | (2006.01) | |
| *G06T 5/40* | (2006.01) | |
| *G06T 5/00* | (2006.01) | |
| *G01D 18/00* | (2006.01) | |

(52) U.S. Cl.
USPC ........... 382/131; 324/309; 324/307; 324/318; 382/128; 382/132; 382/260; 250/252.1

(58) Field of Classification Search .......... 382/128–132; 324/300–322; 600/407–435; 250/252.1
See application file for complete search history.

(56) References Cited

U.S. PATENT DOCUMENTS

| 5,627,907 | A | * | 5/1997 | Gur et al. ....................... 382/132 |
|---|---|---|---|---|
| 5,715,334 | A | * | 2/1998 | Peters ........................... 382/254 |
| 6,956,975 | B2 | * | 10/2005 | Young ........................... 382/263 |
| 7,466,848 | B2 | * | 12/2008 | Metaxas et al. ................. 382/128 |
| 7,627,365 | B2 | * | 12/2009 | Chance ........................... 600/475 |
| 7,630,533 | B2 | * | 12/2009 | Ruth et al. ..................... 382/131 |
| 8,017,906 | B2 | * | 9/2011 | Nelson et al. ............... 250/252.1 |
| 8,131,049 | B2 | * | 3/2012 | Ruth et al. ..................... 382/131 |
| 2002/0181797 | A1 | * | 12/2002 | Young ........................... 382/260 |
| 2005/0027188 | A1 | * | 2/2005 | Metaxas et al. ................. 600/410 |
| 2008/0166035 | A1 | * | 7/2008 | Qian et al. ..................... 382/133 |

(Continued)

FOREIGN PATENT DOCUMENTS

DE 102006021042 10/2007

OTHER PUBLICATIONS

P. Heinlein, J. Drexl, W. Schneider, "Integrated Wavelets for Enhancement of Microcalcifications in Digital Mammography," IEEE Trans. Med. Imaging, vol. 22, No. 3, Mar. 2003.

*Primary Examiner* — Melissa Koval
*Assistant Examiner* — Tiffany Fetzner
(74) *Attorney, Agent, or Firm* — Fletcher Yoder, P.C.

(57) ABSTRACT

A method and apparatus for processing digital mammographic images. The method and apparatus providing comparable mammographic images regardless of the imaging device generating the raw mammographic images. The processed mammographic images may be displayed with optimal global and local contrast, enhanced sharpness, and without the need to apply window level settings or data from lookup tables. A second mammographic image is generated out of a processed first mammographic image in such a way that the projected object, the breast, is more perceptible and obvious for a physician or other medical professional reviewing the mammographic image.

12 Claims, 37 Drawing Sheets

U.S. PATENT DOCUMENTS

| | | | |
|---|---|---|---|
| 2009/0080752 A1* | 3/2009 | Ruth et al. | 382/132 |
| 2009/0185733 A1* | 7/2009 | Heinlein et al. | 382/132 |
| 2010/0086188 A1* | 4/2010 | Ruth et al. | 382/131 |
| 2010/0270462 A1* | 10/2010 | Nelson et al. | 250/252.1 |
| 2011/0142316 A1* | 6/2011 | Wang et al. | 382/131 |
| 2012/0121155 A1* | 5/2012 | Ruth et al. | 382/131 |

* cited by examiner

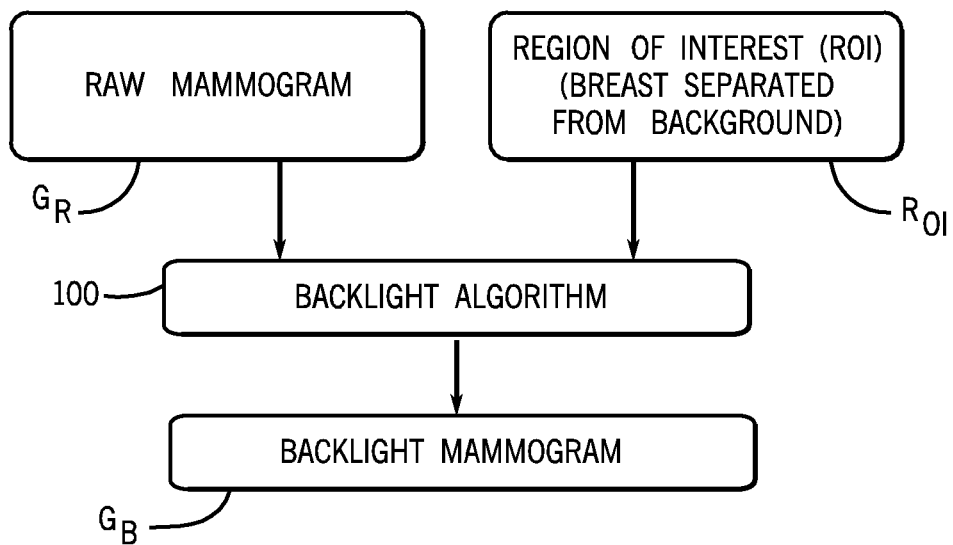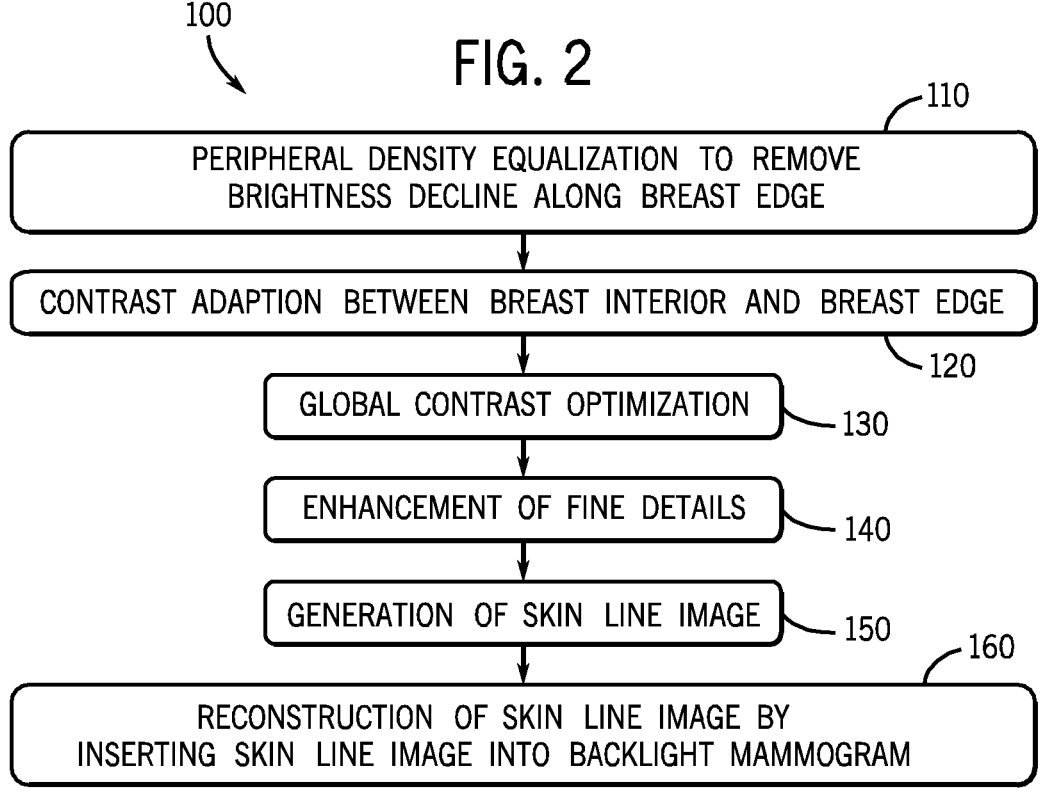

METHOD AND APPARATUS FOR PROCESSING DIGITAL MAMMOGRAPHIC IMAGES WITH PARALLEL MULTI-SCALE DECOMPOSITION AND RECOMBINING IN AN OPTIMIZED MULTI-SCALE RECONSTRUCTION

CROSS-REFERENCE TO RELATED APPLICATIONS

This application claims the benefit of a priority under 35 U.S.C. 119(a)-(d) to German Patent Application No. 102007057013.0, filed Nov. 23, 2007, the entire contents of which are hereby incorporated by reference.

BACKGROUND OF THE INVENTION

This disclosure relates generally to a method and apparatus for processing digital mammographic images.

Digital mammographic images or mammograms are usually presented as gray scale images having individual pixels, with each pixel having a pixel value corresponding to a specific gray scale value. These gray scale values may lie within a range of values between a minimum value of, for example, 0 (black) and a maximum value of, for example, 225 (white). The edge length of a typical mammogram is approximately 2000 to 4000 pixels, and the dissolution of a typical mammogram is approximately 10 line pairs/mm and/or 0.1 mm/pixel.

A mammographic imaging system may be coupled to a workstation, for example, a PACS (Picture Archiving and Communication System) workstation, on which a mammogram may be viewed and reviewed by a physician or other medical professionals. Mammography assigned PACS workstations usually have high resolution monitors, which are able to represent the high volume range and the comparatively high resolution of mammographic images.

Mammographic imaging systems generate raw mammograms containing measured data. These raw mammograms exhibit a global image characteristics with a comparatively high contrast in a boundary region of the measured object (i.e., the boundary region of the breast) and a relatively low contrast inside the measured object (i.e., the inside the breast). Conventional PACS workstations typically include tools for selecting parts of the whole gray scale level range and displaying these parts with maximum contrast through window level settings. Gray scale level ranges outside of the selected gray scale level window are mapped to the smallest or highest possible gray scale level, which means that information contained in these outside ranges is no longer displayed. Alternatively, nonlinear transfer functions represented through so called lookup tables may be applied to the raw mammogram modifying the global image characteristics in order to achieve a better over-all-contrast. Since the available total range of gray scale levels is fixed, a contrast enhancement for a selected part of the gray scale level range leads to a decrease of contrast in other gray level ranges. Therefore, an optimal display of all gray scale levels of the mammogram with optimal contrast and sharpness cannot be achieved by applying window level settings and/or lookup tables.

In order to evaluate the complete dynamic range of a mammogram, multiple window level settings and/or lookup tables are need to be applied, which would consecutively display the various gray scale level ranges, each in an optimal way. However, due to efficiency reasons, this can only be done in exceptional cases.

Most vendors sell their mammographic imaging systems with reviewing workstations that are able to perform processing of raw mammograms, based on the application of lookup tables. Additionally, vendors may include processing algorithms to reduce or remove the typical brightness decline along the breast edge or to increase local contrast in certain regions of the mammogram. The processing procedures of the various vendors may vary considerably in quality and overall impression of the generated images.

The users (physicians or other medical professionals) of these mammographic imaging systems may prefer to have standardized processing methods that work with all the different vendors and different imaging platforms including direct digital platforms, digitized film platforms, and computed radiography (CR) film platforms.

Therefore, there is a need for a method and apparatus for processing mammograms irrespective of the manufacturer of the mammographic imaging system in such a way that the processing improves contrast and sharpness without the necessity for using window level settings and/or lookup tables.

BRIEF DESCRIPTION OF THE INVENTION

In accordance with an aspect of the disclosure, a method for processing a digital mammographic image comprising obtaining a first mammographic image of an object; and processing the first mammographic image to generate a second mammographic image having optimized contrast and improved sharpness as compared to the first mammographic image; wherein the step of processing the first mammographic image comprises removing a brightness decline along an edge of the imaged object; optimizing contrast of the imaged object; and improving visualization of fine details within the imaged object.

In accordance with an aspect of the disclosure, a method for processing digital mammographic images comprising obtaining a first mammographic image of an object, the first mammographic image including raw image data with pixel values assigned to each pixel, the first mammographic image also including a boundary region; balancing a brightness decline in the boundary region of the first mammographic image to produce a brightness-optimized mammographic image; and generating a second mammographic image from the brightness-optimized mammographic image by optimizing the contrast of the pixel values of the brightness-optimized mammographic image and/or optimizing the sharpness of in the imaged object.

In accordance with an aspect of the disclosure, an apparatus for processing digital mammograms comprising means for obtaining a first mammogram of an object, the first mammogram including a boundary region; means for reconciling a brightness decline in the boundary region of the first mammogram; means for generating a brightness-optimized mammogram from different portions of a multi-scale decomposition of the first mammogram, and means for generating a second mammogram having an optimized contrast and an optimized sharpness.

The method and apparatus generates a second mammographic image out of a first mammographic image in such a way that the projected object, the breast, becomes more perceptible and obvious for a physician or other medical professional reviewing the mammogram.

Various other features, aspects, and advantages will be made apparent to those skilled in the art from the accompanying drawings and detailed description thereof.

BRIEF DESCRIPTION OF THE DRAWINGS

FIG. 1 is a summary flow diagram of a method for processing digital mammograms;

FIG. 2 is a more detailed flow diagram illustrating the individual steps of the method of FIG. 1;

DETAILED DESCRIPTION OF THE INVENTION

Figure 3:
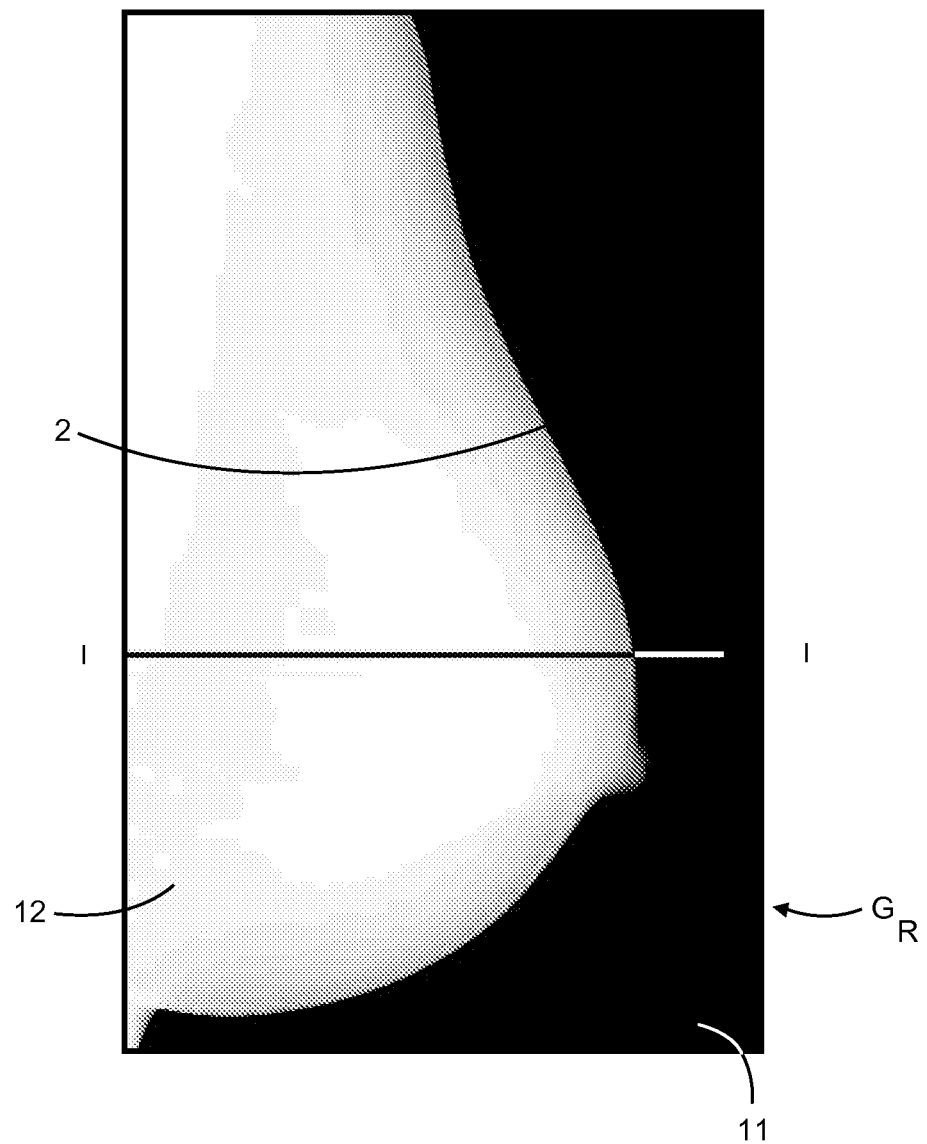
FIG. 3 is a digital mammogram containing raw image data prior to processing.

Referring now to the drawings, FIG. 1 illustrates a summary flow diagram of a method 100 for processing digital mammograms, identified in FIG. 1 as raw mammograms GR. The method 100 may be used on several different imaging platforms, including direct digital platforms, digitized film platforms, and computed radiography (CR) film platforms. A raw mammogram contains original raw image data, captured by an imaging system. The raw mammogram does not include any processing of the raw image data.

The method 100 includes obtaining a mamographic image from a patient and generating a raw mammogram GR, processing the raw mammogram GR with an algorithm 100, and generating a processed mammogram GB. The raw mammogram GR including a region of interest ROI, such as a breast separated from a background. The processing of the raw mammogram GR includes removal of brightness decline along the breast edge, optimization of local contrast, and improved display of fine details of the breast.

The method 100 makes it possible to supply raw mammograms from different imaging platforms and different imaging system manufacturers to yield comparable processed mammographic images in terms of image quality and fine detail. The processed mammographic images may be displayed with optimal global and local contrast, enhanced sharpness, improved representation of the fine detail, and with no need to apply any window level settings and/or lookup table data.

The method 100 generates a second mammographic image from a first mammographic image (raw mammogram) in such a way that the projected object, the breast, becomes more perceptible and obvious for a physician or other medical professional when reviewing the second mammographic image.

The raw mammogram GR contains a number of pixels, with a pixel value assigned to each pixel. The pixel values represent the data measured by the imaging system and provide for visualization of the data in the form of a mammographic image or mammogram of an examined breast. The raw mammogram GR is usually a gray scale image with an edge length of approximately 2000 to 4000 pixels, and a dissolution of approximately 0.1 mm/pixel or 10 line pairs/mm.

The method 100 requires a raw mammogram GR and the projected object or region of interest that includes a determinable outline line separating the breast image from a background image. A method of determining the outline line of a digital mammogram is described in German Patent Application No. 102006021042.

FIG. 2 illustrates a more detailed flow diagram of the individual steps of the method of FIG. 1. In a first step 110, a peripheral density equalization process is performed to remove the brightness decline along the breast edge. In this step, the brightness decline in a boundary region of the mammogram GR between the edge of the breast and the background becomes balanced. In a second step 120, a contrast adaptation process is performed between different regions of the mammogram GR, for example between the breast interior and the breast edge. In a third step 130, a global contrast optimization process is performed to optimize the brightness of the mammogram GR. In a fourth step 140, an enhancement of fine details of the mammogram GR is performed to increase the sharpness of fine structures. In a fifth step 150, a skin line image of the mammogram GR is generated. In a sixth step 160, a reconstruction of the skin line image is performed by adding the skin line image into the mammogram.

A more detailed description of the individual steps 110, 120, 130, 140, 150 and 160 are to be described in the following paragraphs.

In step 110, a reconciliation of the brightness decline in a boundary region along the edge of a breast represented in mammogram GR is performed. This step is described with reference to FIGS. 3-17.

Peripheral density equalization or reconciliation serves to remove the brightness decline arising in the mammogram GR along the edge of the breast. A typical digital mammogram containing raw image data prior to processing is illustrated in FIG. 3. The mammogram GR shows a breast image 12, which clearly stands out against a background 11. The breast image 12 is separated from the background 11 by an outline line 2. Characteristics of the raw mammogram GR show very low contrast within the breast and very high contrast along the edge of the breast.

Figure 4:
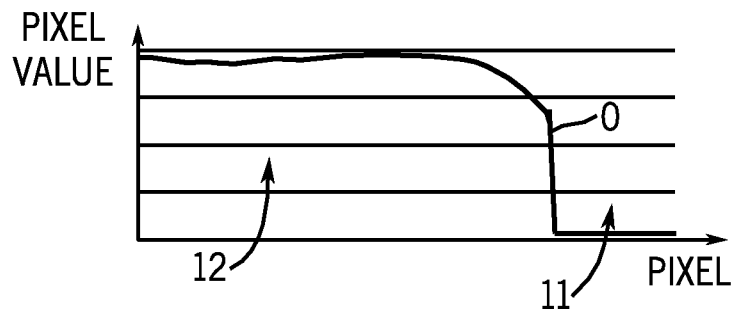
FIG. 4 is a graphical representation of the pixel values of the digital mammogram along line I-I of FIG. 3.

As illustrated in FIG. 4, the brightness of the breast image 12 decreases near the edge of the breast. FIG. 4 illustrates a graphical representation of the pixel values of the mammogram GR along line I-I of FIG. 3. The pixel values along line I-I of FIG. 3 are represented in FIG. 4 as a gray scale pixel value profile O. The gray scale pixel value profile O along line I-I of FIG. 3 shows a typical gray scale pixel value profile, with a decline of the gray scale pixel value towards the edge of the breast. The brightness decline in the boundary region near the edge of the breast is clearly recognizable. The gray scale pixel value profile O shows how the brightness decreases from a certain point to the edge of breast continuously, and then rapidly drops within the range of the skin line. The contrast in the boundary region of the breast image 12 is relatively large, while the contrast inside of the breast image 12 is comparatively small.

In order to accomplish a global optimization of the contrast within the breast image 12, the brightness decline along the edge of the beast image 12 must be eliminated. Subsequently, the gray scale pixel value range can be expanded inside the breast image 12.

In order to remove the brightness decline, the raw mammogram GR is divided into a set of images containing information on various scales by performing a multi-scale decomposition. The multi-scale images are modified independently and afterward recombined to a brightness-optimized mammogram, in which the brightness is globally equalized. The brightness-optimized mammogram may be modified by global contrast and sharpness enhancement algorithms in a comparatively easy way.

By performing a multi-scale decomposition, the raw mammogram GR is divided into a low-pass portion, a high-pass portion and additional band pass filter portions. The low-pass portion contains the low spatial frequencies representing the brightness decline. Therefore, the intention is to remove the low-pass portion representing the main portion of the brightness decline in order to keep the high-pass portion that represents the details of the mammogram.

It is insufficient to decompose the mammogram into only a low-pass and a high-pass portion, since for low limit frequencies the low-pass portion cannot follow the signal discontinuity along the skin line of the breast. All information not contained in the low-pass portion would appear in the high-pass portion and lead to a strong signal overshoot along the edge of the breast. By increasing the limit frequency of the low-pass portion, it would better approximate the signal along the edge of the breast. But the surviving high-pass portion would loose too much information and contain only very fine details. For this reason, the mammogram is decomposed into a low-pass portion, a high-pass portion and additional band pass filter portions.

Figure 5:
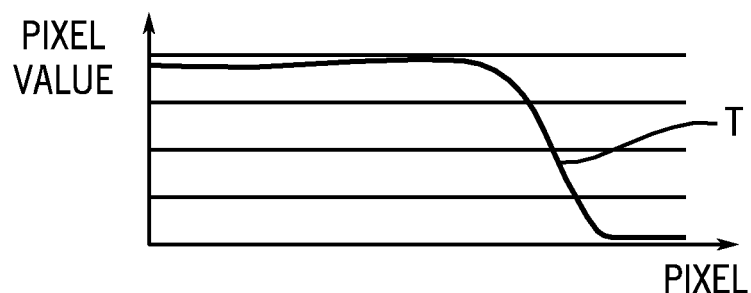
FIG. 5 is a graphical representation of the pixel values of a low-pass portion of the digital mammogram along line I-I of FIG. 3.
Figure 6:
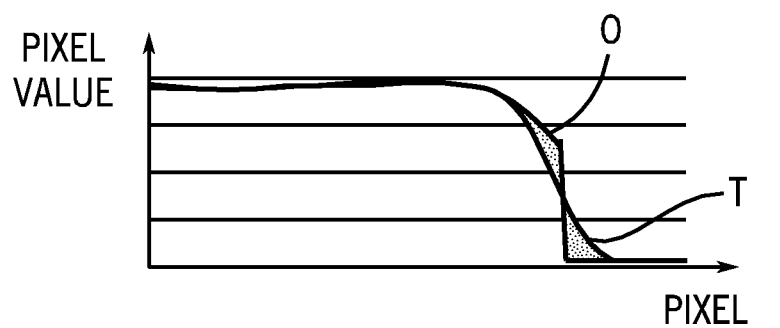
FIG. 6 is an overlaid combined graphical representation of the pixel values of the digital mammogram and low-pass portion along line I-I of FIG. 3.
Figure 7:
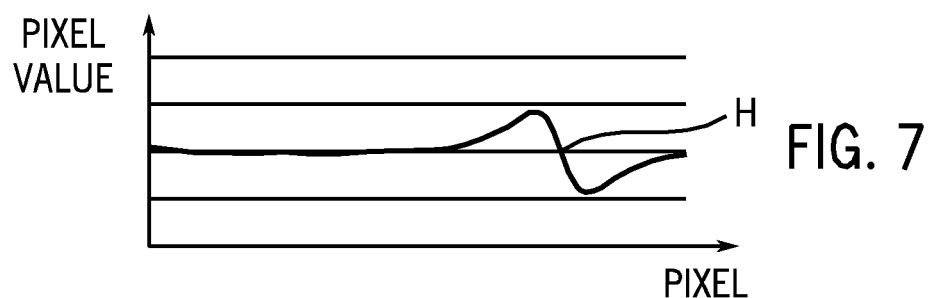
FIG. 7 is a graphical representation of the pixel values of a high-pass portion of the digital mammogram along line I-I of FIG. 3.

FIG. 5 illustrates a graphical representation of the pixel values of a low-pass portion of the digital mammogram GR along line I-I of FIG. 3, represented by the gray scale pixel value low-pass portion profile T. FIG. 6 illustrates an overlaid combined graphical representation of the original gray value profile O and the low-pass profile T. FIG. 7 illustrates a graphical representation of the pixel values of a high-pass portion of the digital mammogram GR along line I-I of FIG. 3, represented by the gray scale pixel value high-pass portion profile H.

The multi-scale decomposition divides the mammogram GR into a low-pass portion T, four band-pass filter portions of B1, B2, B3, B4, and a high-pass portion H. The different portions T, H, B1, B2, B3, B4 are independently modified and reconstructed to a brightness-optimized mammogram in which the brightness decline is balanced in the boundary region of the breast.

It should be pointed out that a different decomposition may be applied, in particular, a decomposition of more or less than four band-pass filter portions is possible. The parameters of the decomposition, in particular the number of band-pass filter portions and the exact critical frequencies of the low-pass, band pass, and high-pass portions are dependent on the desired result, and may be varied and optimized.

Figure 8A:
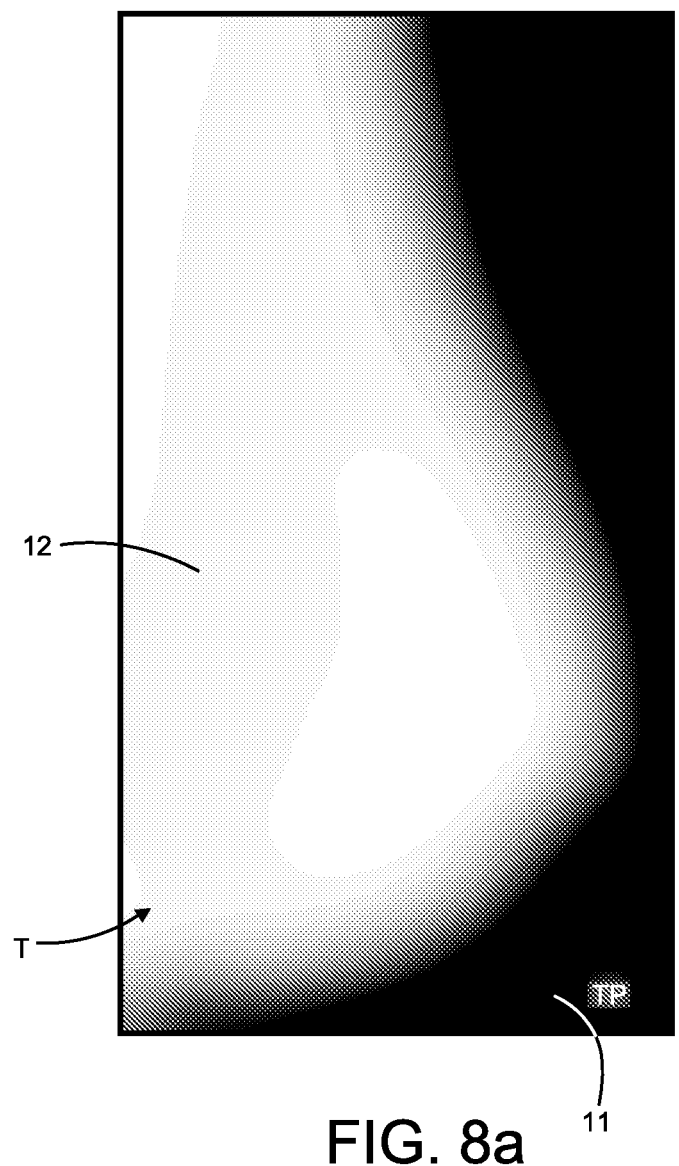
FIG. 8a is a gray scale pixel value figurative representation of the low-pass portion.
Figure 8B:
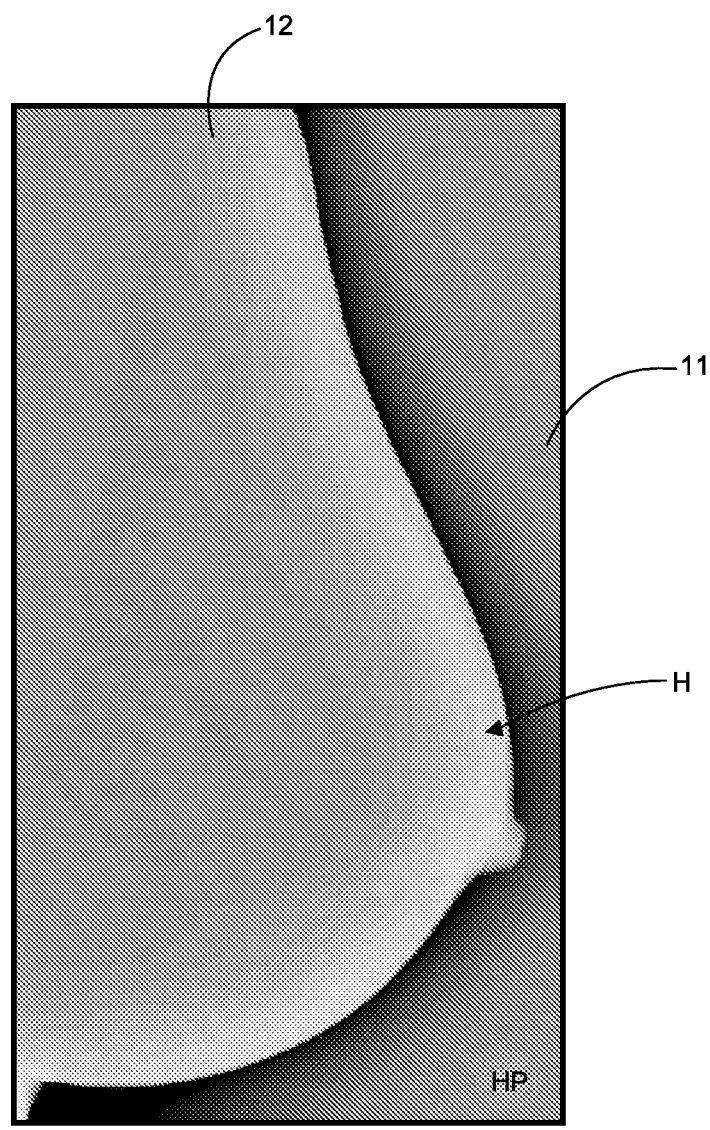
FIG. 8b is a gray scale pixel value figurative representation of the high-pass portion.

FIG. 8a illustrates a gray scale pixel value figurative representation of the low-pass portion T. FIG. 8b is a gray scale pixel value figurative representation of the high-pass portion H. An overshoot is clearly evident in the brightness of the high-pass portion H, shown in FIG. 8b, along the boundary region of the breast.

Figure 9A:
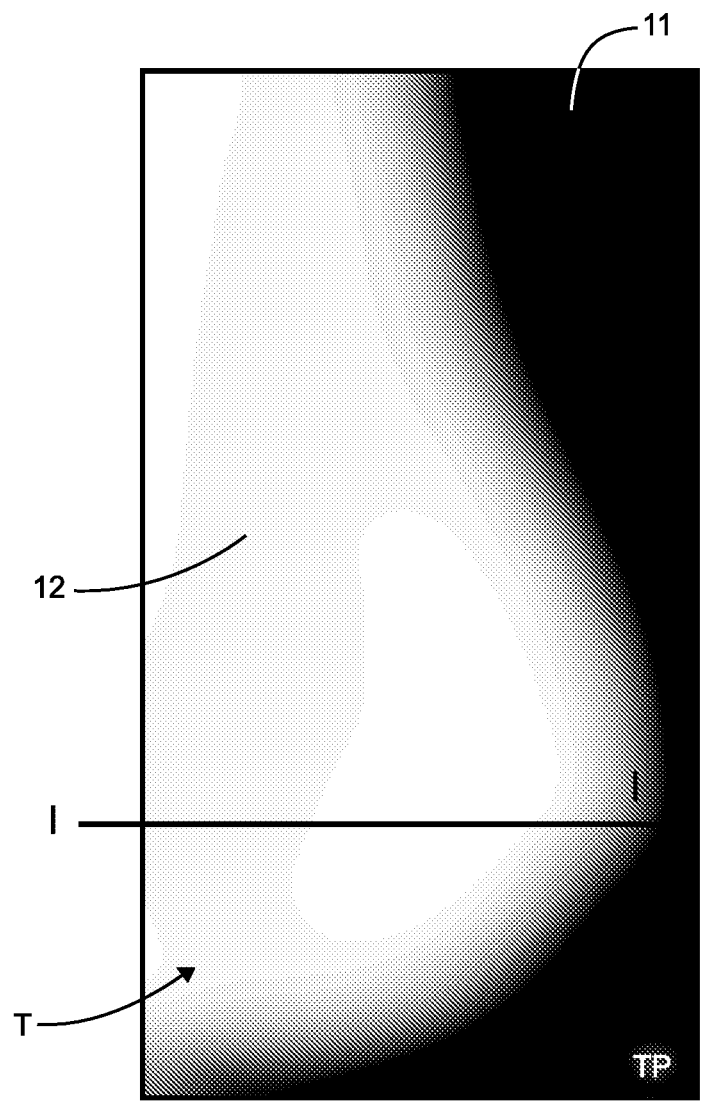
FIGS. 9a-9f are gray scale pixel value figurative representations of the portions of a multi-scale decomposition.
Figure 9B:
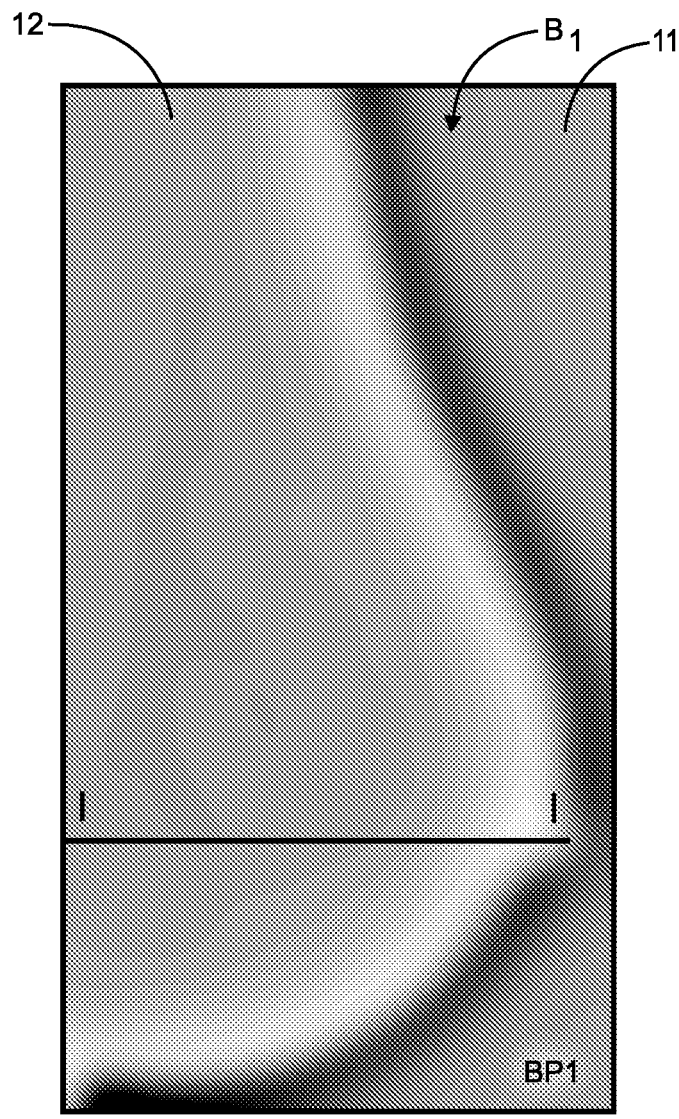
Figure 9C:
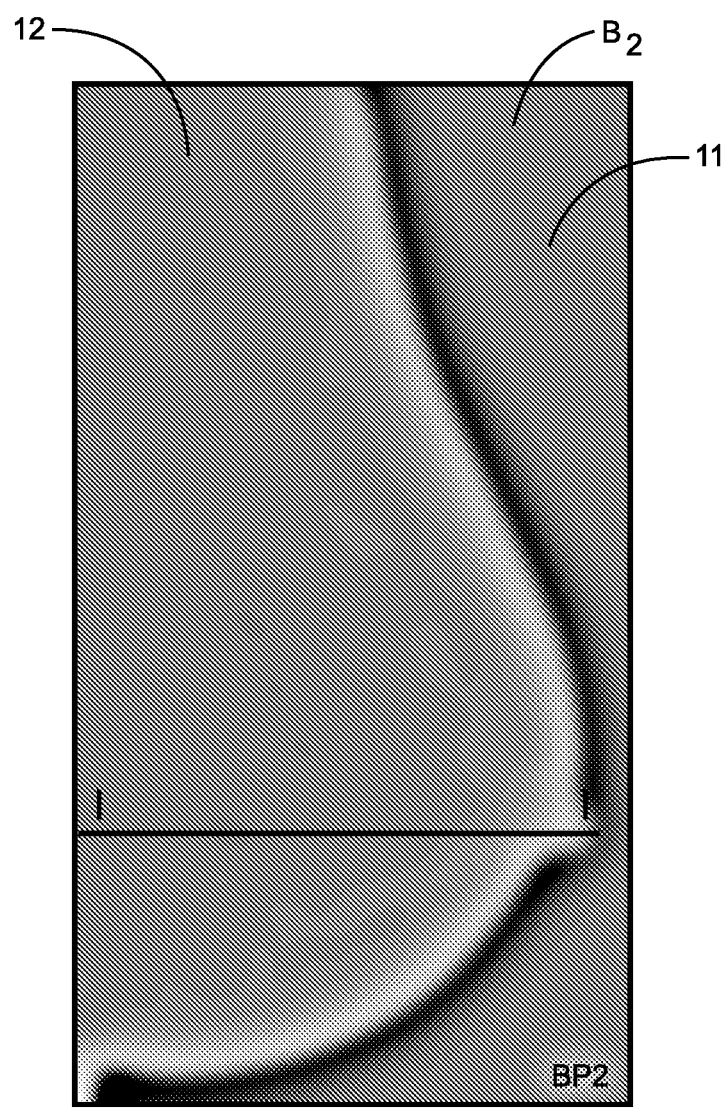
Figure 9D:
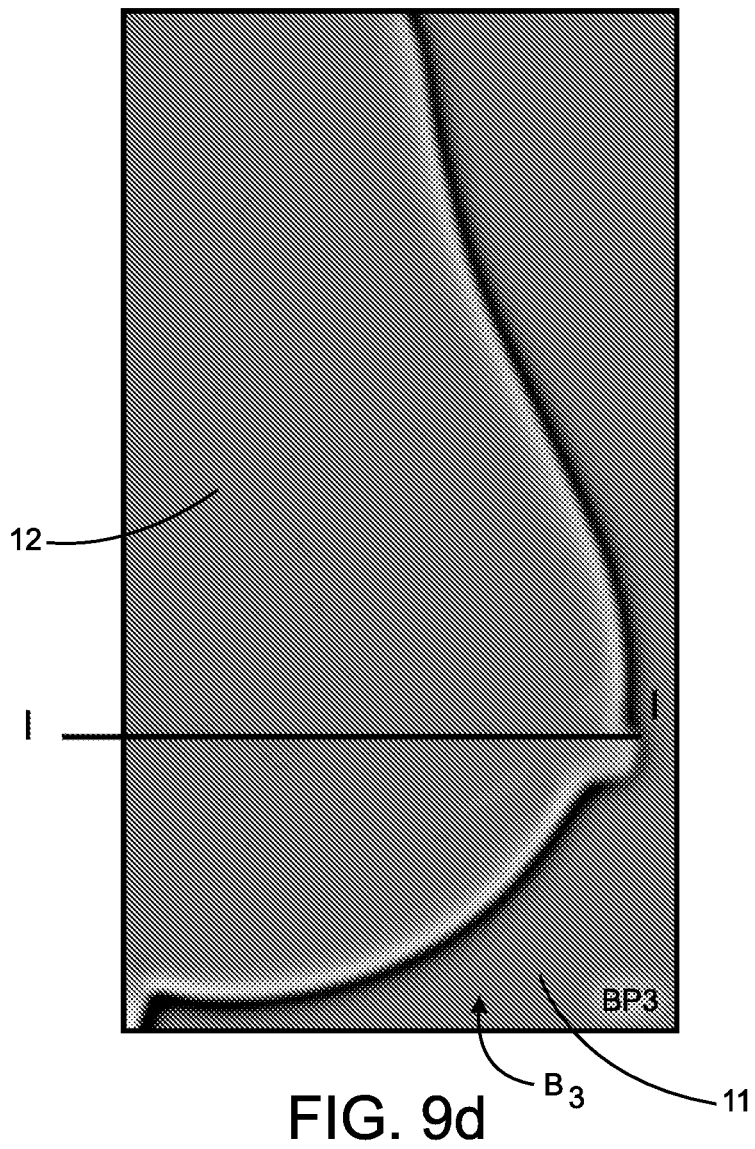
Figure 9E:
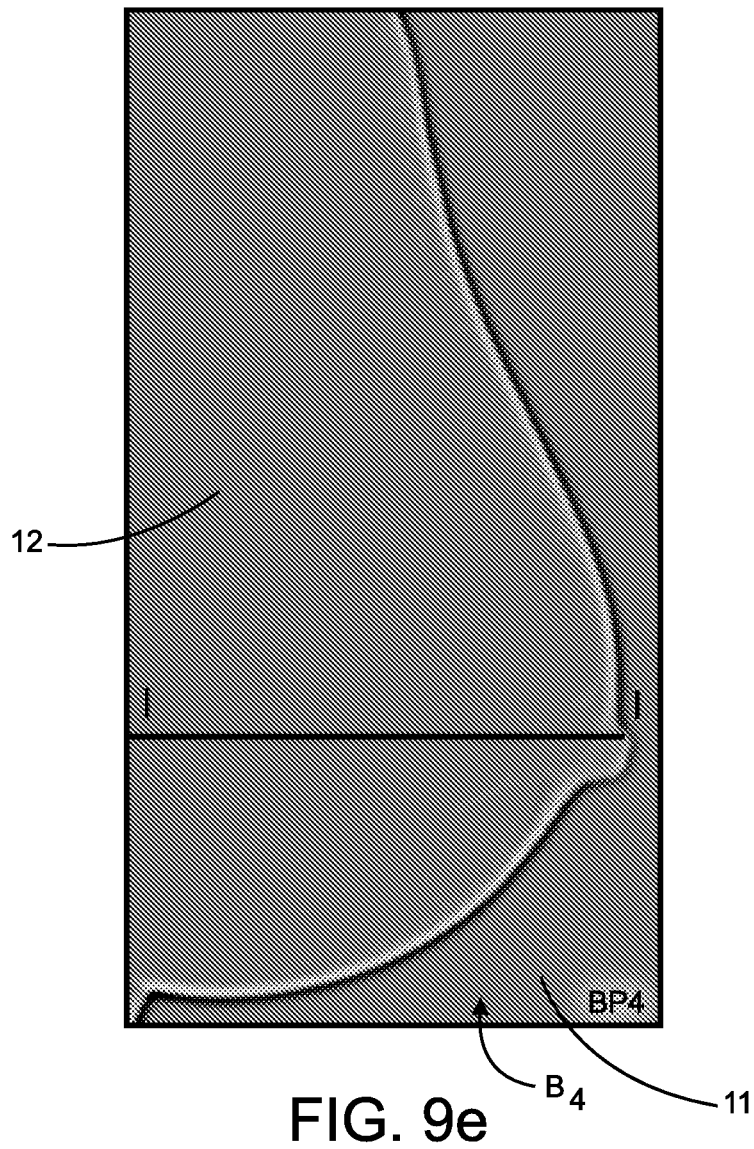
Figure 9F:
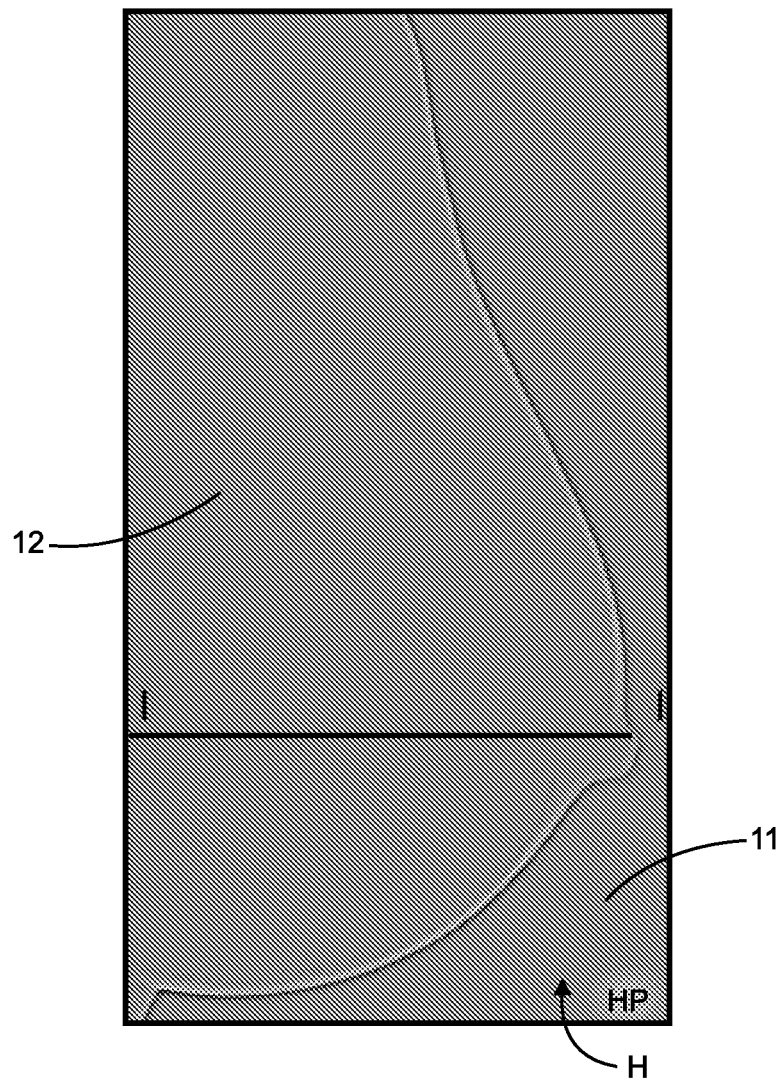

FIGS. 9a-9f illustrate gray scale pixel value figurative representations of the portions of a multi-scale decomposition for removing brightness decline. Each figure shows the breast image 12 and the background 11. FIG. 9a represents the low-pass portion T, FIGS. 9b-9e represent the band pass filter portions B1, B2, B3, B4, and FIG. 9f represents the high-pass portion H. Each of the band pass filter portions B1, B2, B3, B4 and the high-pass portion H contain an overshoot signal portion, since no fraction can follow the signal singularity at the skin line perfectly.

Figure 10A:
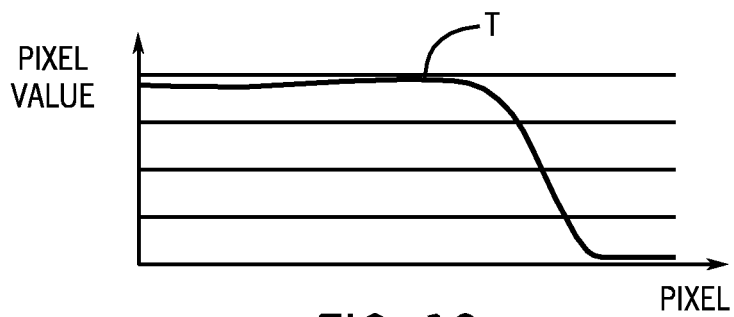
FIGS. 10a-10f are graphical representations of the pixel values of the portions of the multi-scale decomposition along lines I-I of FIGS. 9a-9f.
Figure 10B:
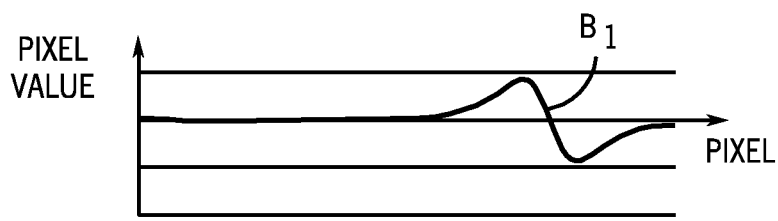
Figure 10C:
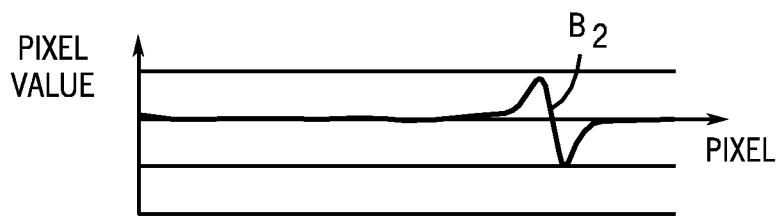
Figure 10D:
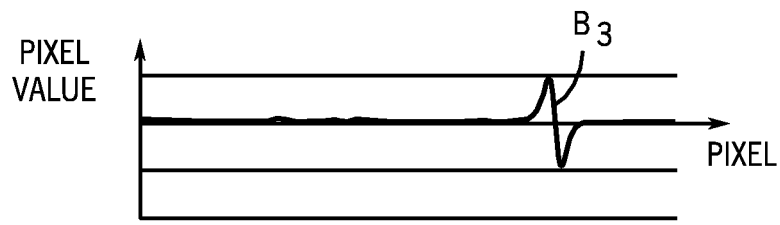
Figure 10E:
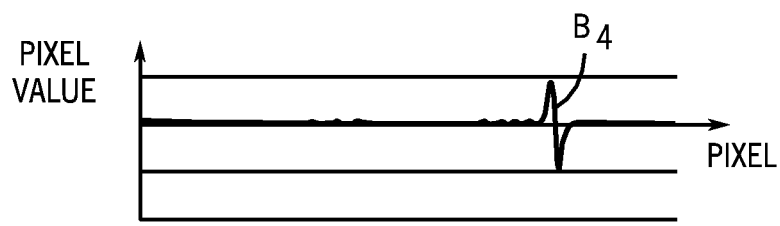
Figure 10F:
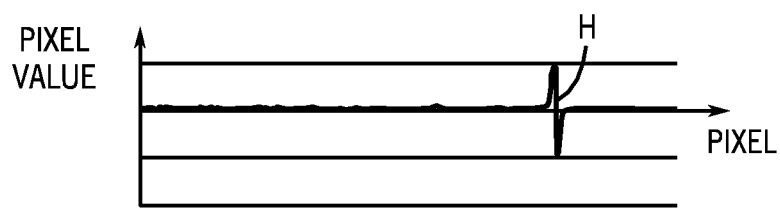

FIGS. 10a-10f illustrate graphical representations of the pixel values of the portions of the multi-scale decomposition along lines I-I of FIGS. 9a-9f. FIG. 10a represents the low-pass portion profile T, FIGS. 10b-10e represent the band pass filter portion profiles B1, B2, B3, B4, and FIG. 10f represents the high-pass portion profile H. Each of the band pass filter portion profiles B1, B2, B3, B4 and the high-pass portion profile H contain an overshoot signal portion. The low frequencies have a relatively large overshoot width, while the high frequencies have a relatively small overshoot width.

It is evident that the overshoot width depends on the structural width of the individual filters (i.e., their critical frequencies). The overshoot width may be determined on the basis of each filter computationally.

The first band-pass filter portion B1 may have a structural width of approximately 16 mm to 35 mm. For each following band-pass filter portions B2, B3, B4 their structural widths are halved, so that the second band-pass filter portion structural width may be approximately 8 mm to 16 mm, the third band-pass filter portion B3 structural width may be approximately 4 mm to 8 mm, and the fourth band-pass filter portion B4 structural width may be approximately 2 mm to 4 mm. The high-pass portion H structural width may be approximately 2 mm or smaller. The low-pass portion T exhibits all signal portions with a structural width of greater than 35 mm.

Figure 11:
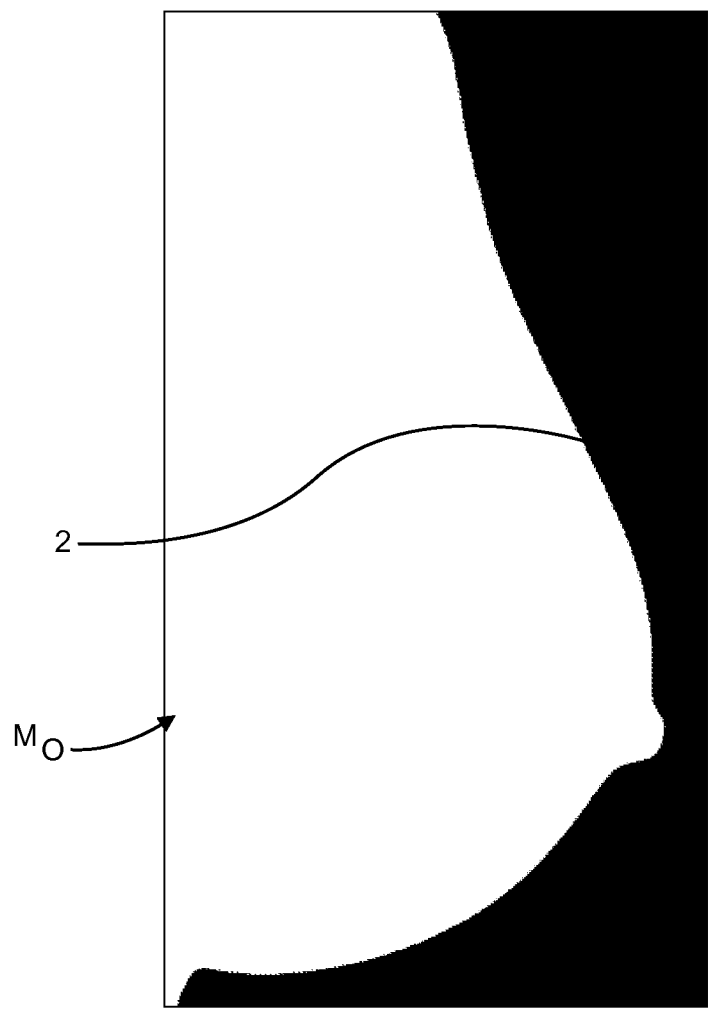
FIG. 11 is a figurative representation of a mask representing a region of interest.
Figure 12A:
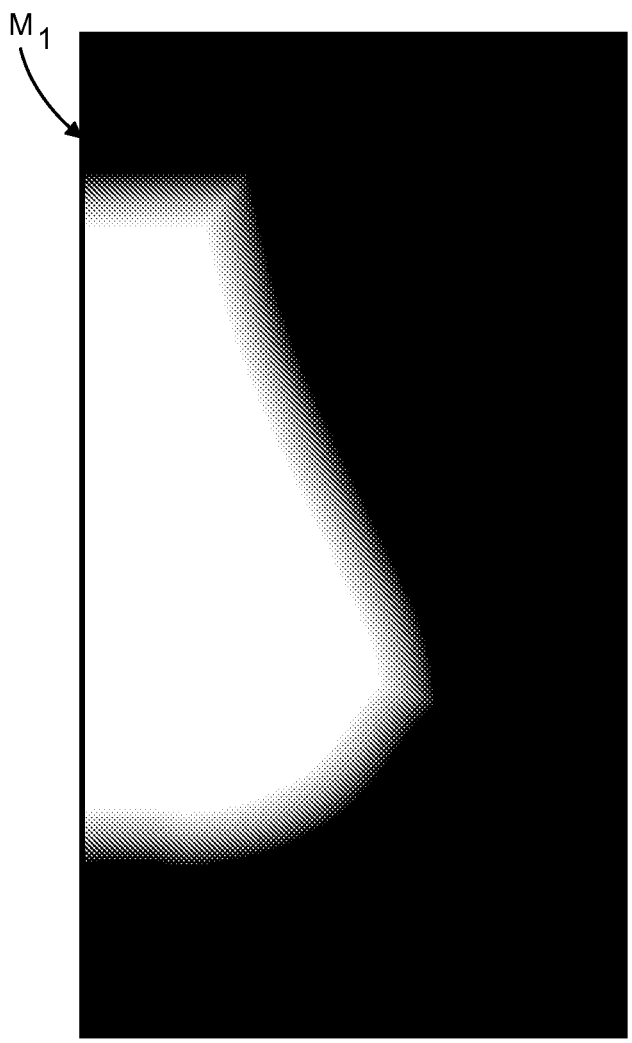
FIGS. 12a-12e are figurative representations of masks for modification of the portions of the multi-scale decomposition of FIGS. 10b-10f.
Figure 12B:
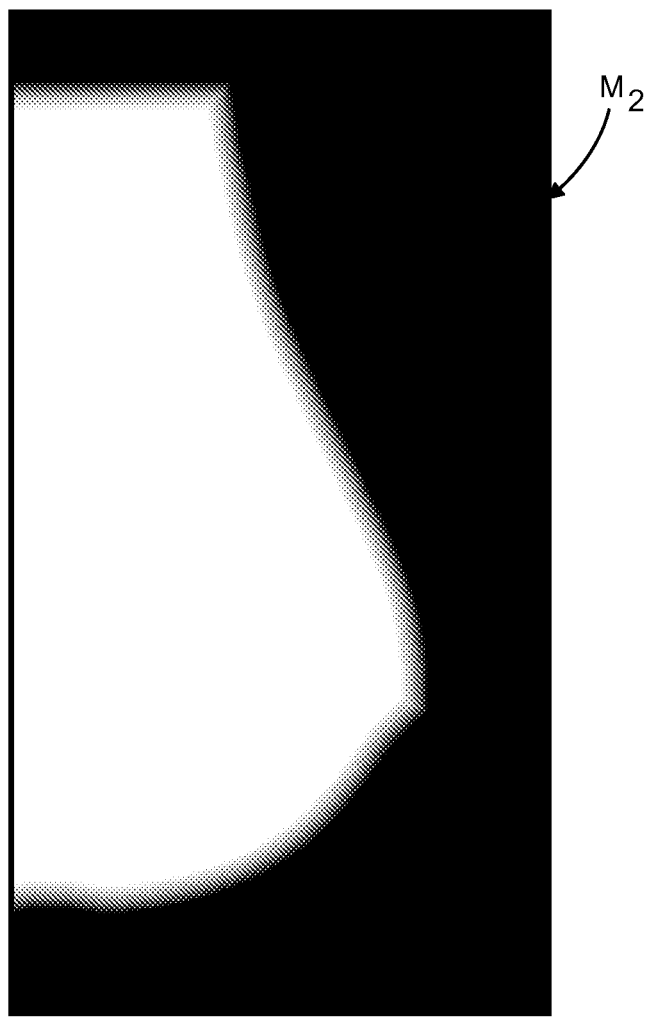
Figure 12C:
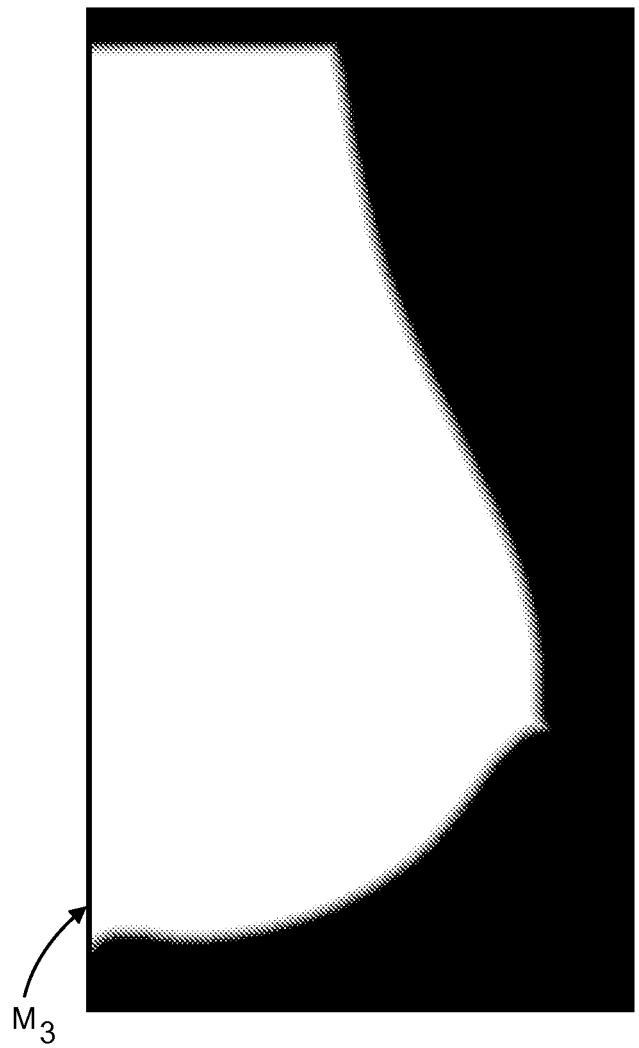
Figure 12D:
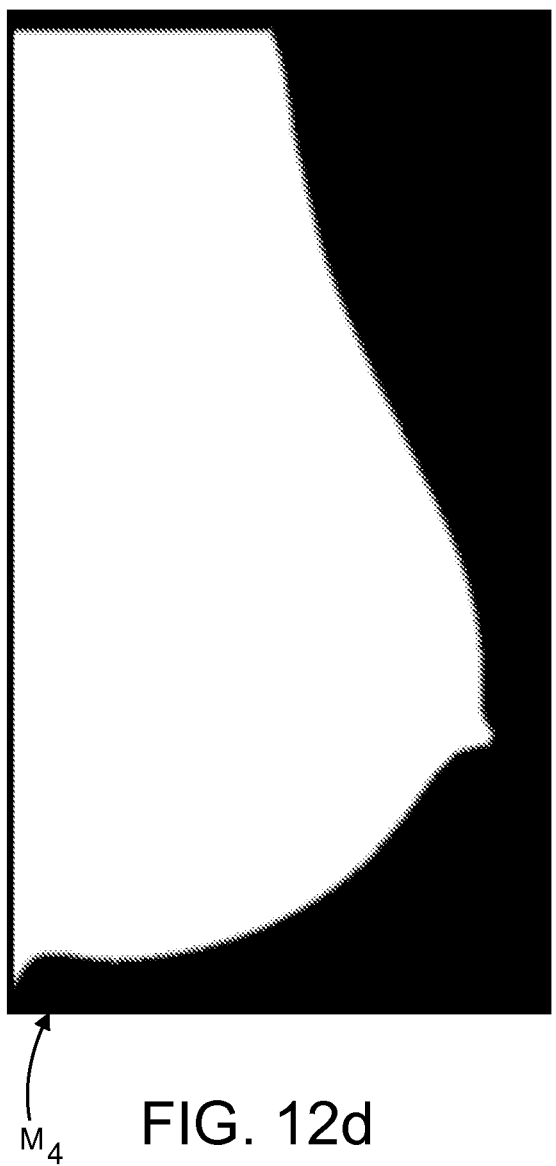
Figure 12E:
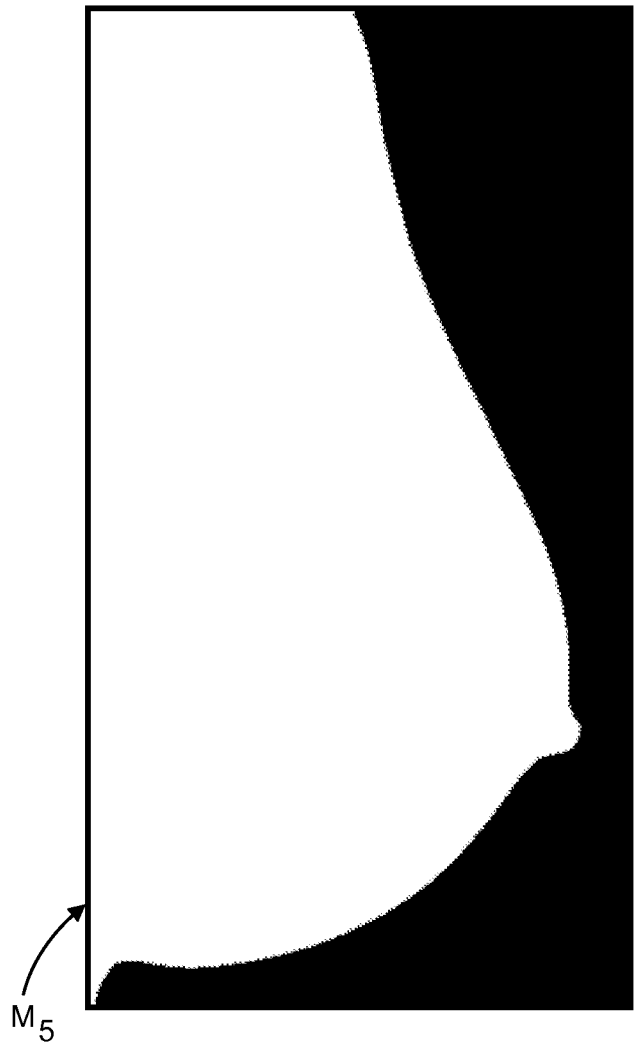
Figure 13A:
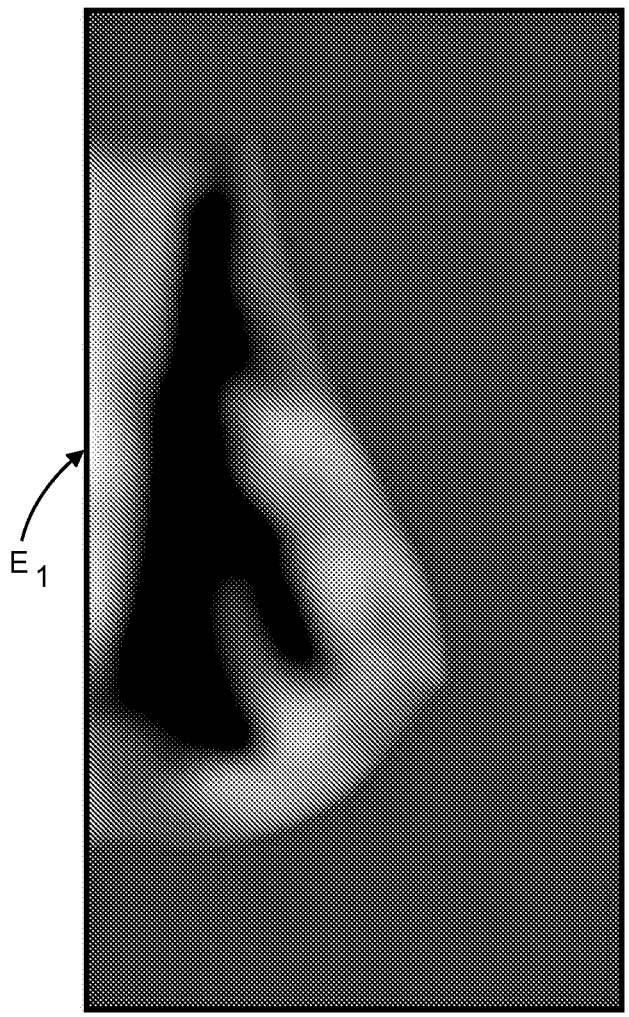
FIGS. 13a-13e are gray scale pixel value figurative representations of the modified portions of FIGS. 12a-12e.
Figure 13B:
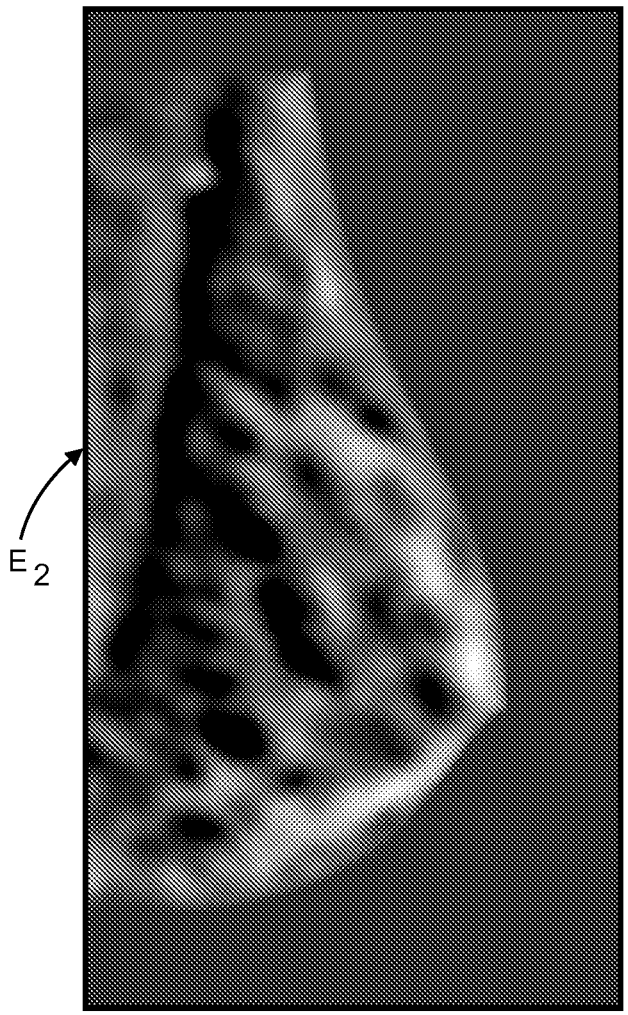
Figure 13C:
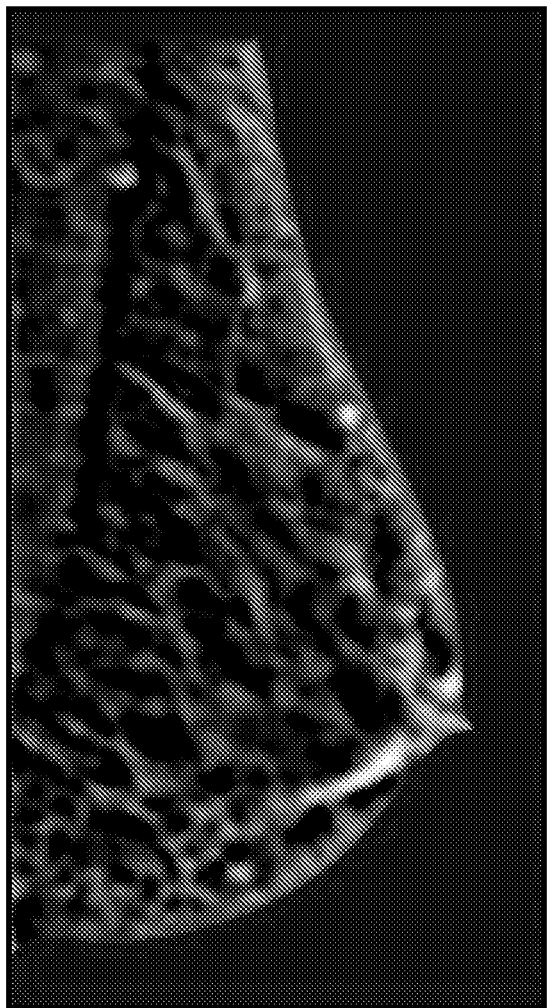
Figure 13D:
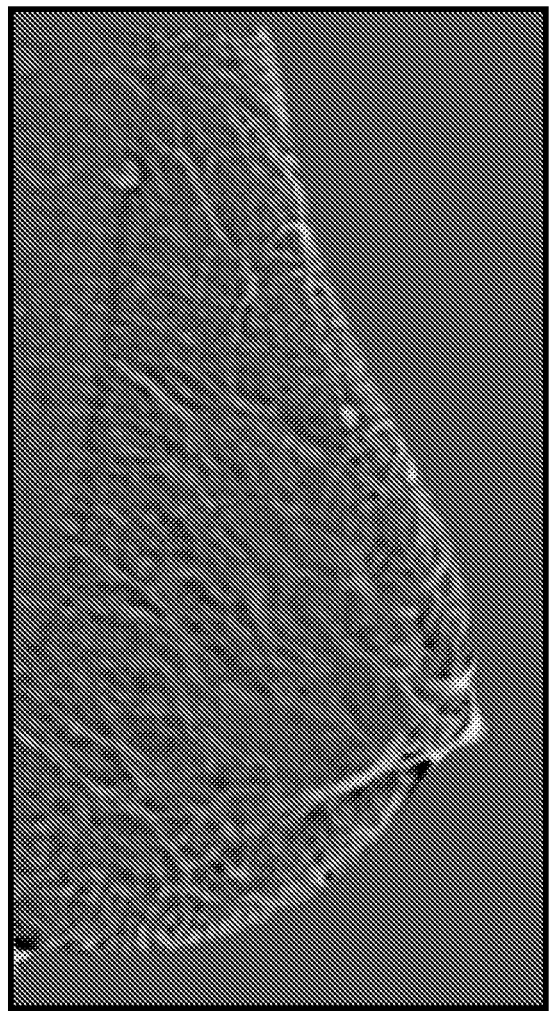
Figure 13E:

FIG. 11 illustrates a figurative representation of a mask M0 representing a region of interest. An outline line 2 of the imaged object (breast) is shown.

The brightness decline in mammogram GR is eliminated by reconstruction of the multi-scale images in the band-pass filter portions B1, B2, B3, B4 and high-pass portion H after the overshoot is removed from each multi-scale image. Mask M0 in the imaged object area (breast) has pixel values set to 1 (white), while the background 11 has pixel values set to 0 (black).

From mask M0, band-pass filter portions B2, B3, B4 and high-pass portion H become for each portion of B1, a mask M5, in which the original object area along outline line 2 around the width of the overshoot region of each band pass filter portion B1, B2, B3, B4 and high-pass portion H are eroded except for the low-pass portion T. In each case, a mask M1, M2, M3, M4 is generated where the outline line is shifted the width of the overshoot region toward the inside the breast.

In order to avoid reconstruction artifacts, the eroded edges are faded out, whereby the width of the faded out ranges depend on the structural width of the respective portions B1, B2, B3, B4, H. In such a way, masks M1, M2, M3, M4, M5 are produced as shown in FIGS. 12a to 12e. FIGS. 12a-12e are figurative representations of masks M1, M2, M3, M4, M5 for modification of the portions of the multi-scale decomposition of FIGS. 10b-10f. Each mask image M1, M2, M3, M4 is derived from a binary image which contains white pixels within the breast area and black pixels in the background. For each band-pass filter portion B1, B2, B3, B4 and the high-pass portion H, an erosion is performed on the mask image. The erosion width is equivalent to the width of the overshoot region in each band-pass filter portion B1, B2, B3, B4 and the high-pass portion H.

Each band-pass filter portion B1, B2, B3, B4 and the high-pass portion H are multiplied by the associated masks M1, M2, M3, M4, whereby the overshoot region in the individual band pass filter portions B1, B2, B3, B4 and high-pass filter portion H are eliminated, resulting in the images E1, E2, E3, E4, E5 of FIGS. 13a to 13e. After multiplying the band-pass filter portion B1, B2, B3, B4 and the high-pass portion H with the eroded mask image, the overshoot region is removed. After that, a reconstruction is performed with the modified band-pass filter portion B1, B2, B3, B4 and the high-pass portion H.

FIGS. 13a-13e illustrate gray scale pixel value figurative representations of the modified portions of FIGS. 12a-12e. FIGS. 13a-13e show the eroded region of interest masks E1, E2, E3, E4, E5 for each scale image B1, B2, B3, B4 and H. Multiplying the band-pass filter portion B1, B2, B3, B4 and the high-pass portion H with eroded region of interest masks removes the overshoot areas and a display of higher contrast is possible.

Figure 14:
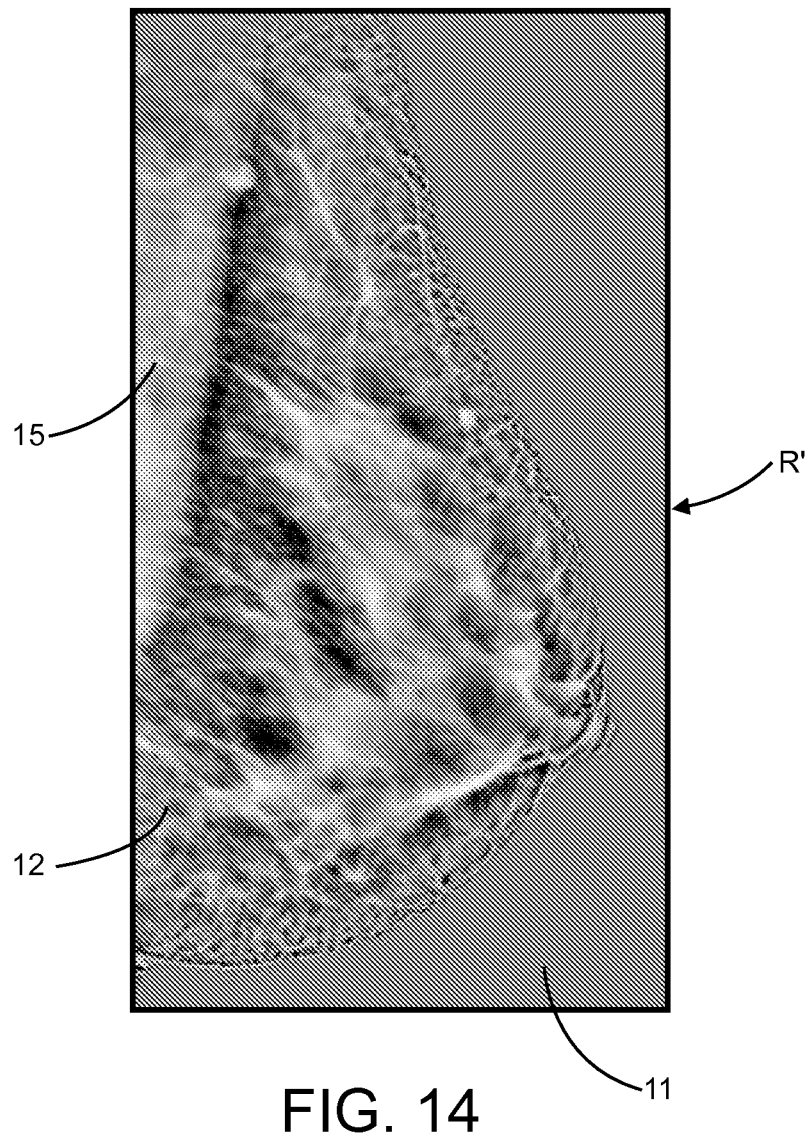
FIG. 14 is a reconstructed mammogram image without the low-pass portion.

FIG. 14 illustrates a reconstructed mammogram image R' without the low-pass portion T. This mammogram may be called a brightness optimized mammogram. By setting the low-pass portion T to zero (which means the low pass portion T is totally eliminated), the reconstruction generates an image without any brightness decline at the breast edge. But the mammogram will only contain structures smaller than the width corresponding with the limit frequency of the low pass portion T, and will not look like a typical mammogram (dependent on the critical frequency of the low-pass portion of T).

This reconstructed image R' shows all details, the brightless decline is removed, and application of window level settings is not necessary. However, the image R' does not look like a typical mammogram, the musculus pectoralis 15 and dense breast tissue are not well separated from fat tissue, and there is too high contrast along the edge of the breast.

In order to achieve a mammogram containing structures with a greater width, at least to a certain degree, the low pass portion T should not be eliminated, but modified by subtracting a threshold from all low pass pixels and setting all negative pixels to 0.

Figure 15A:
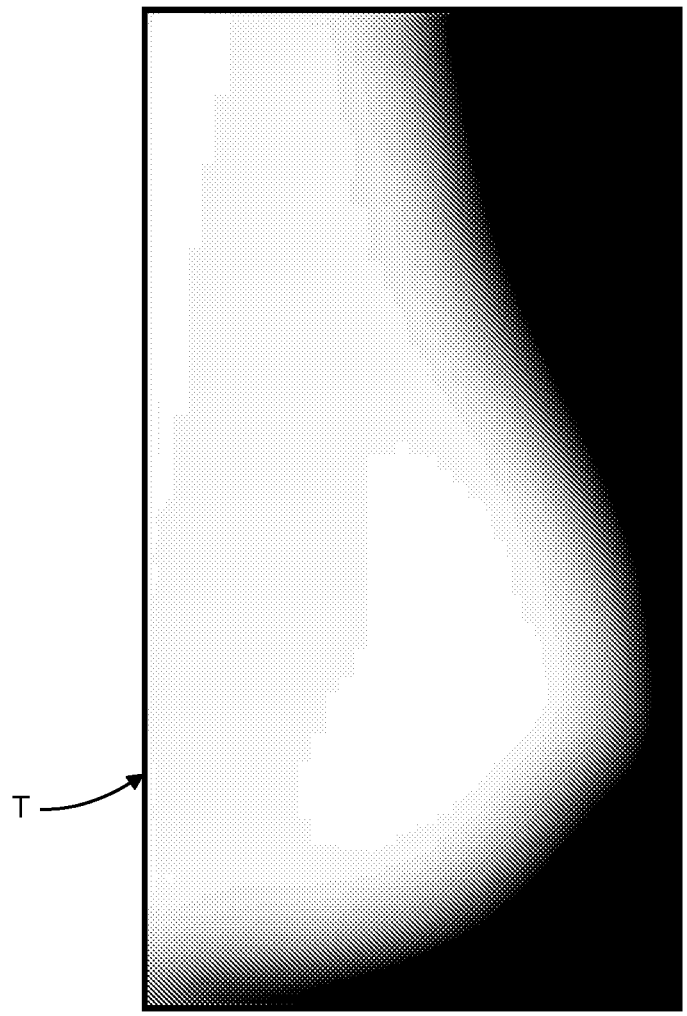
FIG. 15a is a gray scale pixel value figurative representation of the low-pass portion.
Figure 15B:
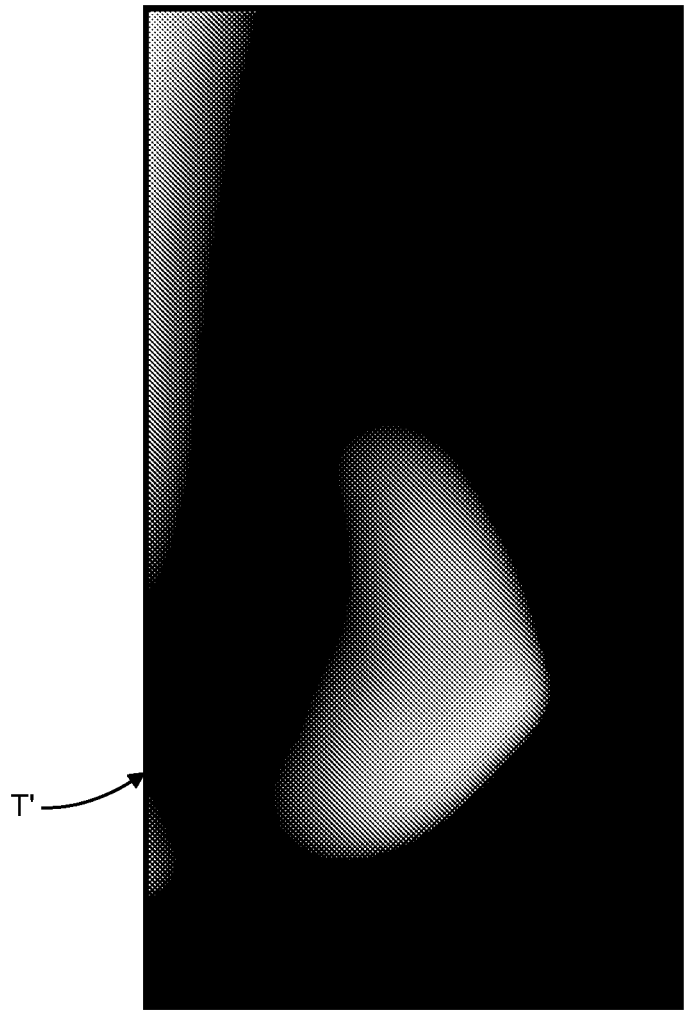
FIG. 15b is a gray scale pixel value figurative representation of a modified low-pass portion.

FIG. 15a illustrates a gray scale pixel value figurative representation of the low-pass portion T. FIG. 15b illustrates a gray scale pixel value figurative representation of a modified low-pass portion T'. The low-pass portion of T is modified. A histogram is computed. From this histogram, a median is determined. This median is subtracted from the low-pass portion T, and all negative pixel values are set to 0. Before the reconstruction the modified low-pass portion T' is multiplied by a scaling factor, in order to absorb its influence in relation to the band-pass filter portions of B1, B2, B3, B4 and the high-pass portion of H.

Figure 16:
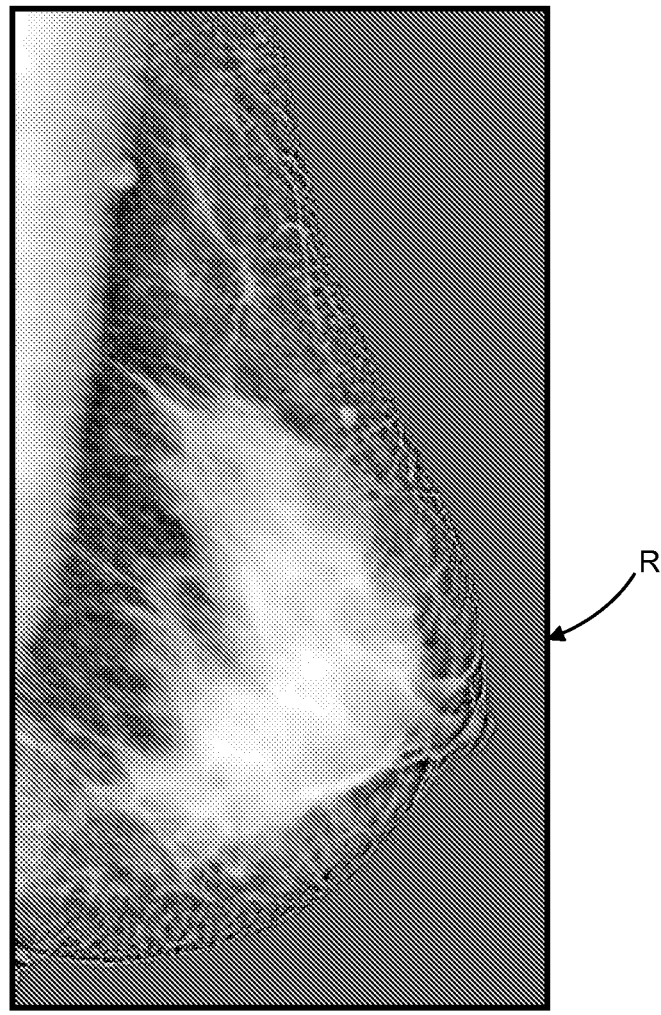
FIG. 16 is a reconstructed mammogram image with a modified low-pass portion.
Figure 17:
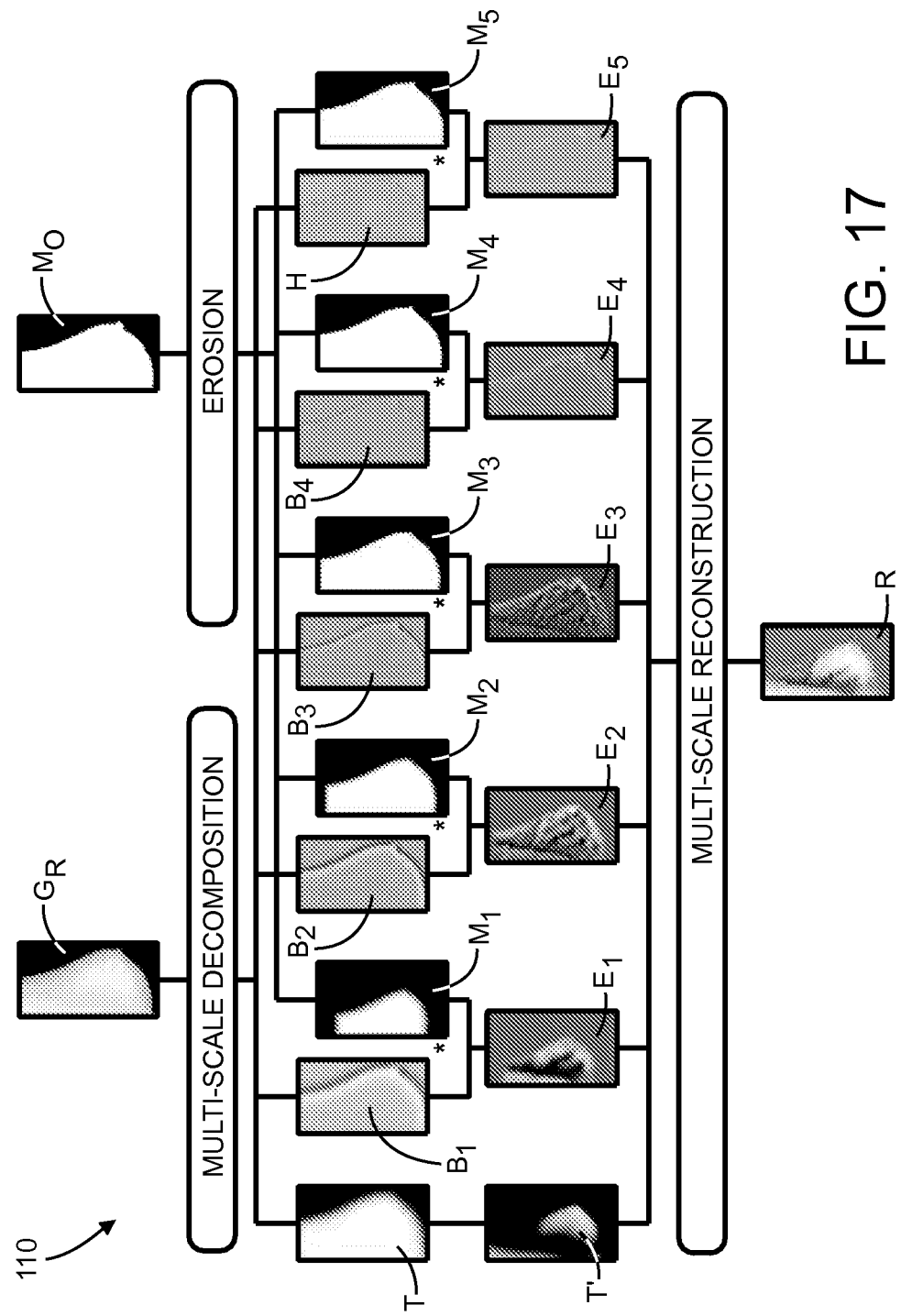
FIG. 17 is a summary presentation of the steps for removing brightness decline.

The result is a brightness-optimized mammogram R as shown in FIG. 16, that also contains large structures, which allows for the distinction of muscle and areas of dense tissue from areas of fat tissue. The brightness decline remains eliminated. FIG. 16 illustrates the reconstructed mammogram image R including the modified low-pass portion T'. FIG. 17 illustrates a summary presentation of the steps for removing brightness decline.

Figure 18:
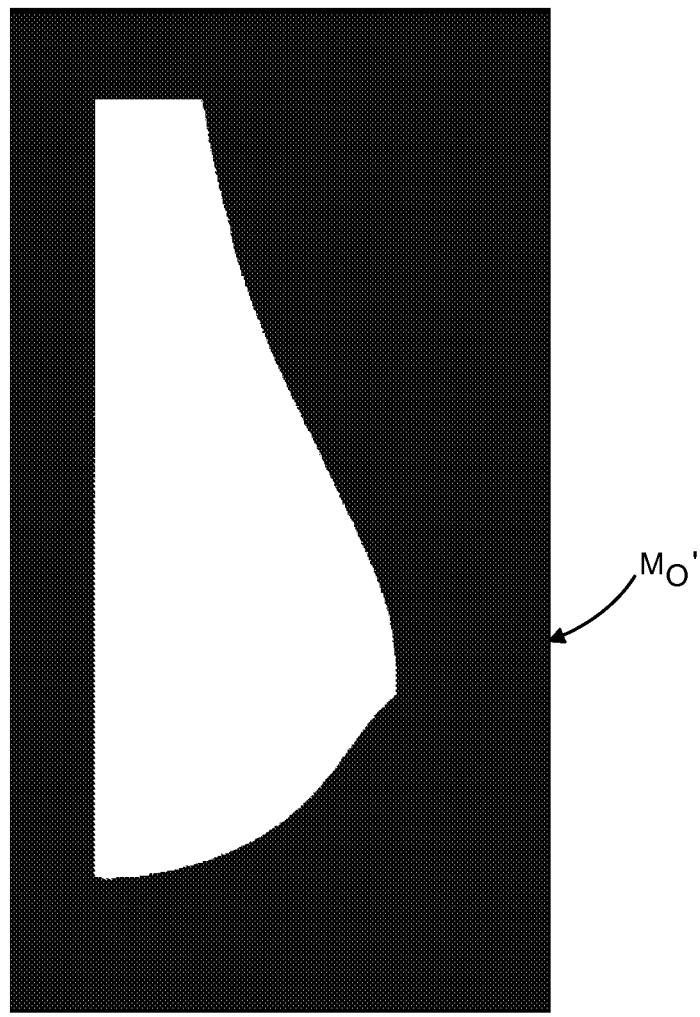
FIG. 18 is a figurative representation of a mask for determination of an interior region of an imaged object for contrast adaption.
Figure 19:
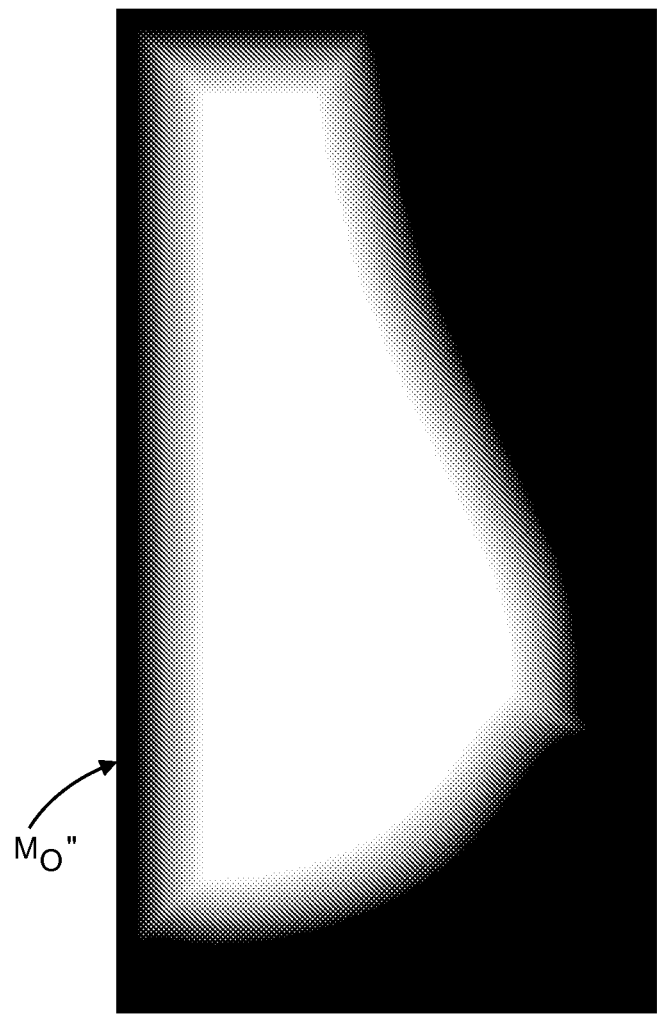
FIG. 19 is a gray scale pixel value figurative representation of a mask for production of a modified high-pass portion for contrast adaption.

In step 120, a reconciliation of the contrast between the breast interior and the breast edge is performed (contrast adaption). This step is described with reference to FIGS. 18 and 19. FIG. 18 illustrates a figurative representation of a mask M0' for determination of an interior or central region of an imaged object (breast) for contrast adaption. FIG. 19 illustrates a gray scale pixel value figurative representation of a mask M0" for production of a modified high-pass portion for contrast adaption.

The modifications so far, however, may lead to a different contrast within the breast edge region compared with the contrast in the central breast region. This effect is removed by adapting the contrast along the breast edge to the contrast within the central region.

After reconciliation of the brightness decline the pixel values in the outside boundary region exhibit generally a higher dispersion than the pixel values inside the breast. These dispersions are adapted together.

In order to adapt the dispersions, first the dispersions of the pixel values in a central site become estimated. The definition of the central site becomes the mask M0 of the object area, a further mask M0' is generated that erodes the object area of all edges by a certain amount.

The reconstructed mammogram R available after the reconciliation of the brightness decline in the boundary region is divided into a high-pass portion and a low-pass portion. The high-pass portion contains small or fine structures, while the low-pass portion contains larger structures. The fine structures in the high-pass portion may be regarded as dispersions of the pixel values around the process contained in the low-pass portion. As a dispersion measure, the absolute value of the pixel values of the high-pass portion are averaged over a range from approx. 16 $mm^2$. This dispersion measure is computed for all pixels within the central region and averaged. A global dispersion is performed in which the dispersions of the pixel values in the boundary region are to be adapted.

In order to adapt the dispersions in the boundary region, a copy of the high-pass portion is made whose pixel values are modified, if the local dispersion measure is larger than 16 mm² a large environment of pixels, a global middle dispersion measure is determined within the central site. The pixel value is multiplied by the quotient from that middle dispersion measure and the dispersion measure of the pixel environment.

From the original high-pass portion, a modified high-pass portion is generated with the help of a cross fade mask. Afterwards, reconstruction is accomplished. The cross fade mask M0" is produced from mask M0' by adding a certain amount of fading. The cross fade mask M0" contains values between zero and one, whereby the pixel values of the cross fade mask M0" determine the portions of the original high-pass portion and the modified high-pass portion. The larger the pixel value of mask M0", the more influence by the original high-pass portion; the smaller the pixel value of mask M0", the more influence by the modified high pass portion.

Now the modified high-pass portion and the low-pass portion are reconstructed. After reconstruction a mammogram is generated, with which the dispersion of the pixel values in the breast boundary region corresponds to the dispersion of the pixel values in the central site of the breast.

In step 130, a global contrast optimization is performed. Having a brightness-optimized mammogram without brightness decline along the breast edge, a global contrast optimization can be performed on the image. For this, a gamma correction is applied to all pixels within the projected breast, which moves the median of the gray value distribution of these pixels to a pre-defined value. This generates comparable mammograms with nearly equivalent overall contrast impressions.

The goal is for all mammograms to have comparable contrast. The gamma correction is applied having a harmonious character that offers the advantage of a histogram balance procedure that those remains inherent dynamics, i.e., a proportional relationship from close gland fabric to surrounded fatty tissue in the mammogram. The gamma value is determined dynamically from the mammogram and selected after transformation of the median of all pixel values corresponding to a value within the breast range grw.

$$grw = grwmin + 0.3(grwmax - grwmin)$$

Where grwmin is the minimum value of all pixel values within the breast range and grwmax is the maximum value.

The gamma value is computed by:

$$gamma = \log(grw)/\log(median)$$

Where median corresponds to the median of all pixel values within the breast range before the gamma transformation.

The gamma correction takes place, in all pixel values g of the mammogram according to the formula:

$$gneu = grwmin + ((g-grwmin)/(grwmax-grwmin))^{gamma} \cdot (grwmax - grwmin)$$

The next step in the process is enhancement of fine details in order to produce a mammogram with increased sharpness. In step 140, an optimization of the sharpness of the fine structures is performed. This step is described with reference to FIGS. 20a, 20b, 21 and 22.

Again, the image undergoes a multi-scale decomposition, which separates it into several portions containing structures at different scales. The weights of each band pass and the high-pass portion are slightly raised by application of a moderate gamma correction. The multi-scale reconstruction of the modified portions creates a mammogram with enhanced sharpness.

Figure 20B:
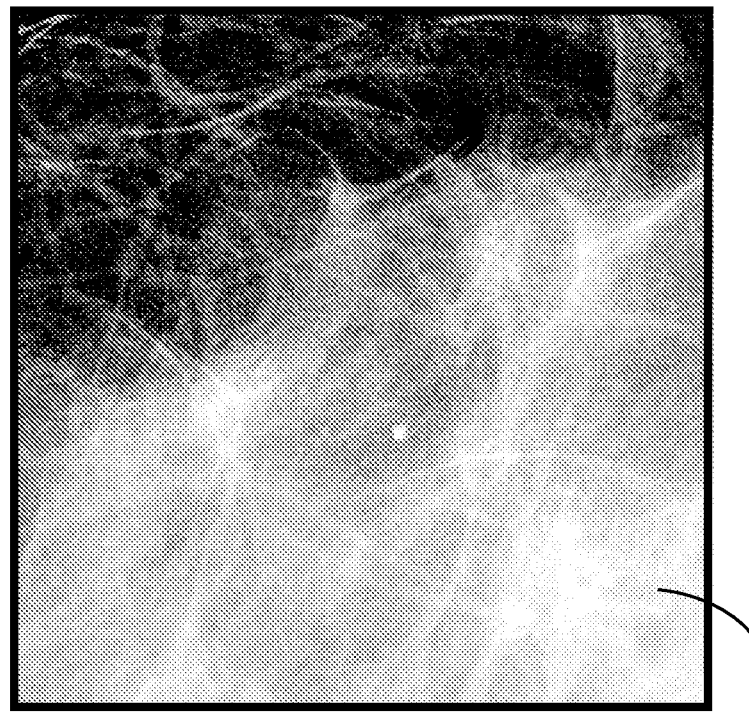
FIG. 20b is a gray scale pixel value figurative representation of a cutout of a mammogram after enhancement of fine details.
Figure 20A:
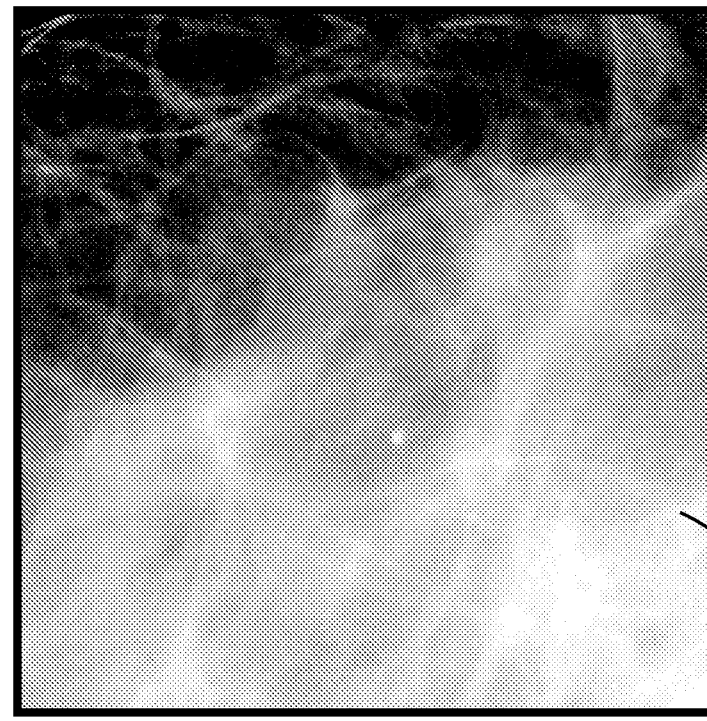
FIG. 20a is a gray scale pixel value figurative representation of a cutout of a mammogram before enhancement of fine details.

FIG. 20a illustrates a gray scale pixel value figurative representation of a cutout of a mammogram before enhancement of fine details (optimization of the sharpness of shown structures). FIG. 20b illustrates a gray scale pixel value figurative representation of a cutout of a mammogram after enhancement of fine details (optimization of the sharpness of shown structures).

Figure 21:
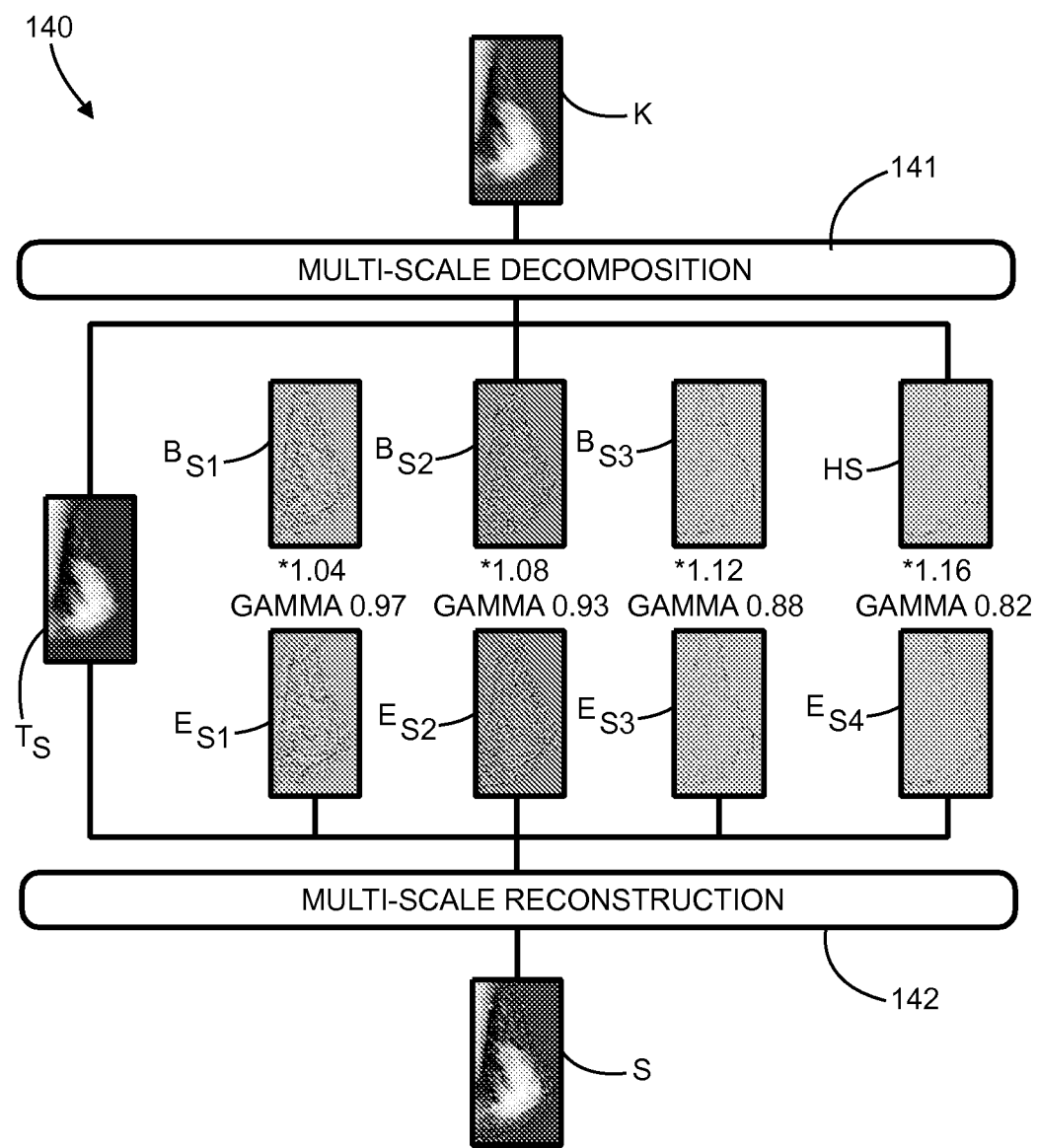
FIG. 21 is a summary presentation of the steps for enhancement of fine details.

FIG. 21 illustrates a summary presentation of the steps for enhancement of fine details. For optimization of the sharpness of shown structures, a renewed multi-scale decomposition 141 is accomplished, dividing mammogram K, already contrast-optimized, into a low-pass portion TS, band-pass filter portions BS1, BS2, BS3 and high-pass portion HS. The roughest structures contained in band-pass filter portion BS1 are dimensioned in such a way that the corresponding structural width is approximately 4 mm. The structural widths of the following band-pass filter portions BS2, BS3 and high-pass portion of HS are scaled around a factor 2 in each case.

The band-pass filter portions BS1, BS2, BS3 and high-pass portion HS are strengthened altogether by multiplication of their pixel values with a factor, whereby this factor for the band-pass filter BS1 amounts to 1.04 and for each further portion BS2, BS3, and HS around 0.04 to 1.08, 1.12 and 1.16. The individual portions BS1, BS2, BS3, HS are applied with a gamma correction (gamma values between 0.97 and 0.82), so that the pixels with smaller pixel values are easily revalued opposite those with higher pixel values. The low-pass portion is not changed.

After modification of the band-pass filter portions BS1, BS2, BS3 and high-pass portion HS, a multi-scale reconstruction 142 is accomplished. The result being a sharpened mammogram S as shown in FIG. 22.

Figure 22:
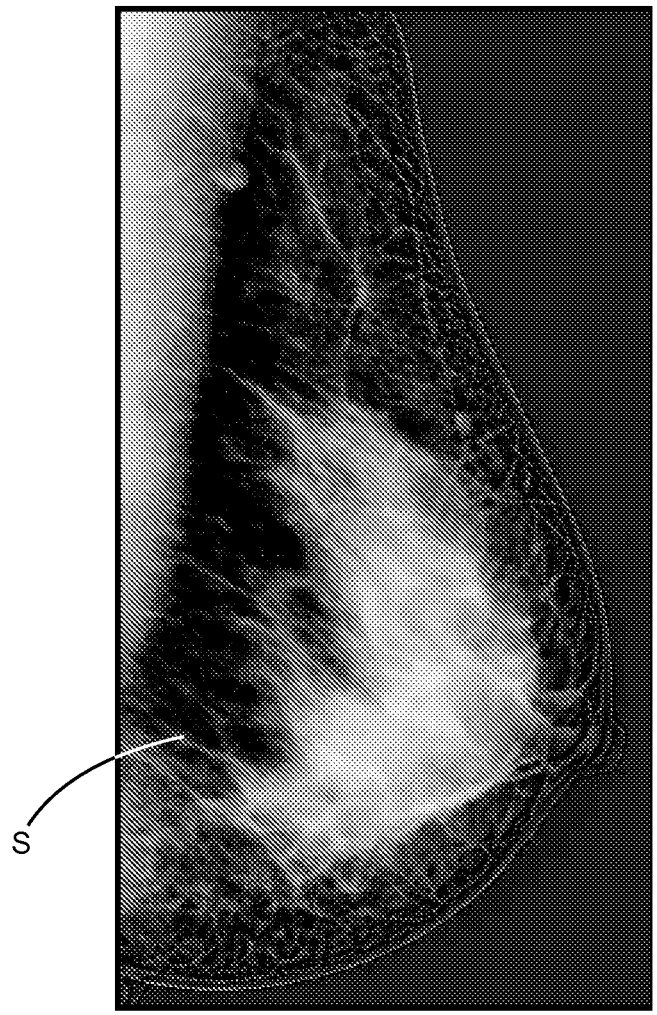
FIG. 22 is a gray scale pixel value figurative representation of a mammogram after enhancement of fine details without a skin line.

FIG. 22 illustrates a gray scale pixel value figurative representation of a mammogram S after enhancement of fine details without a skin line. During the process used to remove the brightness decline along the breast edge, each band and high pass was GE multiplied with an eroded mask image. Thus, the skin line was cut off from the projected mamma.

In step 150, generation of a skin line image is performed. This step is described with reference to FIG. 23.

As mentioned previously, after steps 110 thru 140, the contrast and sharpness are missing from optimized mammogram S along the edge of the breast, which corresponds to the skin line. The skin line image is generated in step 150, from the original mammogram GR, FIG. 3, which contains a skin line.

The skin line lies straight in the range of the original mammograms GR with the strongest brightness decline. In order to be able to recognize this global brightness decline overlaid fine structures, the mammogram GR is gradient filtered. However, only the boundary region of the breast is gradient filtered, not the entire mammogram GR. The internal area of the breast is left alone, in order to adjust the contrast of the skin line image and optimize the contrast and sharpness of mammogram S.

Among the boundary region of the breast all pixels are ranked according to pixels having pixel values below a threshold value. The threshold value is selected in such a way that the sum of the surface portions of the pixel values constitutes smaller than a threshold value that is a third of the comprehensive breast area. For the entire boundary region the threshold value is taken off. The pixel values in the boundary region are replaced by gradient values, whereby the gradient values are the differences between the pixel values of a mammogram, which was produced by filtering of the original mammograms with a 1 mm² large average value filter, in which pixel values of the original mammograms GR result.

Figure 23:
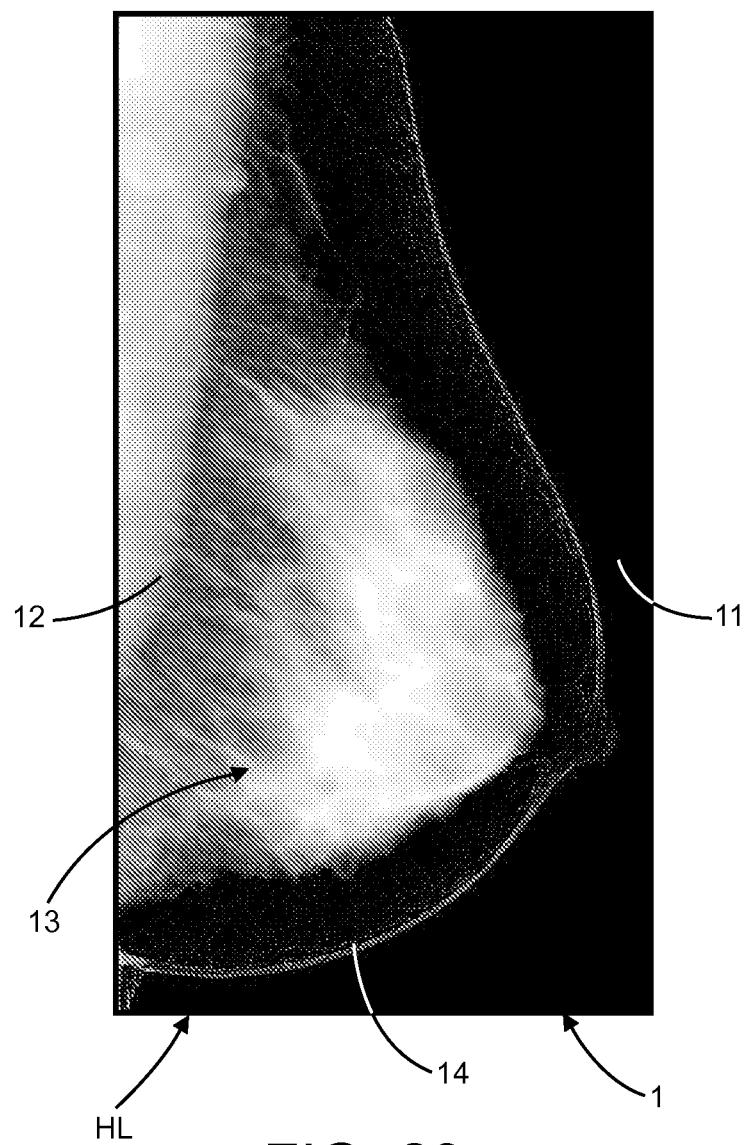
FIG. 23 is a gray scale pixel value figurative representation of a gradient-filtered mammogram produced from the original digital mammogram.

In such a manner, a skin line image HL is generated as shown in FIG. 23. FIG. 23 illustrates a gray scale pixel value figurative representation of a gradient-filtered mammogram produced from the original digital mammogram.

Figure 24:
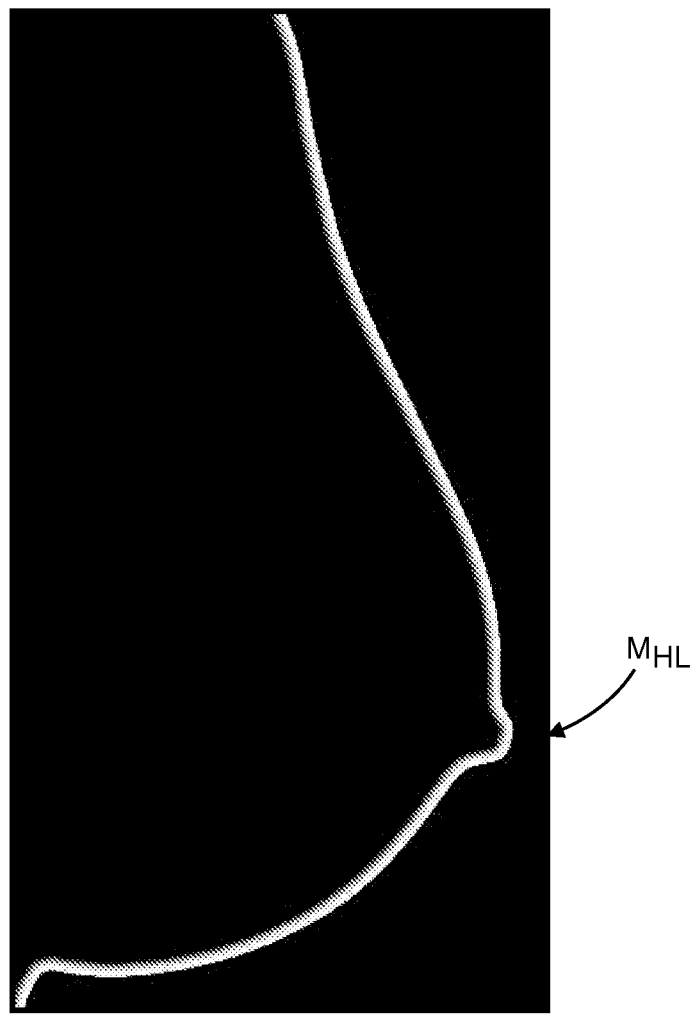
FIG. 24 is a figurative representation of a mask for extraction of the skin line from the mammogram of FIG. 23.
Figure 25:
FIG. 25 is a gray scale pixel value figurative representation of a processed mammogram in accordance with the disclosed method and apparatus.

In step 160, a reconstruction of the skin line image is performed. This step is described with reference to FIGS. 24-25. FIG. 24 illustrates a figurative representation of a mask for extraction of the skin line from the mammogram of FIG. 23. FIG. 25 illustrates a gray scale pixel value figurative representation of a processed mammogram in accordance with the disclosed method and apparatus.

The last step of the method is reconstruction of the skin line image and adding the reconstructed skin line image to the mammogram. The skin line to be reconstructed is taken from a gradient filtered version of the original mammogram. A fading mask containing a bright line along the breast edge, which is faded towards the breast interior, is used to control the amount of information taken from the gradient filtered image and inserted into the generated mammogram. The central regions of the mamma remain unchanged after the skin line reconstruction.

The skin line contained in the skin line image must be transferred into mammogram S. Since by application of process steps 110 thru 150, the ranges of values can have changed in mammogram S and the skin line image HL in relation to the original range of values. Thus, the two mammograms S and HL must be re-adapted together.

The skin line reconstruction takes place via a mask-controlled cross fade. In addition, a skin line mask MHL derived from mask M0 of the object area generates a copy of the mask M0 and is inverted, where the white range (pixel value 1) of the inverted mask M0 are expanded about around 1 mm outward and fades out around 3 mm outward. The skin line mask MHL for the cross fade results from multiplication of the skin line image HL with the original mask M0. The skin line mask MHL is shown in FIG. 24.

The skin line mask MHL and the mammogram S are then joined together. The pixel values in the skin line mask MHL determine to what extent the pixel values of a contrast and sharpen-optimized mammogram of S are absorbed and replaced by pixel values from the skin line image. Within the range of the skin line the pixel value of the skin line mask MHL equals one, and in the internal area of the breast the pixel value of skin line mask MHL equals zero.

The result is a contrast and sharpness optimized, and skin line containing, processed Mammogram GB as shown in FIG. 25. It is clear that the processed mammogram GB is improved, with uniformly large contrast inside the breast and also shows structures inside the breast with increased sharpness compared to the original mammogram GR as shown in FIG. 3. The processed mammogram GB may now be reviewed by a physician or any other medical professional. An additional processing by means of window level settings or lookup tables is not necessary.

While the disclosure has been described with reference to various embodiments, those skilled in the art will appreciate that certain substitutions, alterations and omissions may be made to the embodiments without departing from the spirit of the disclosure. In particular other parameters for the multi-scale decompositions and transformations may be used and optimized according to the application. The parameters, for example, the critical frequencies for the portions of the different multi-scale decompositions are to be understood as examples only and do not completely exclude the use of different parameter combinations. Accordingly, the foregoing description is meant to be exemplary only, and should not limit the scope of the disclosure as set forth in the following claims.

What is claimed is:

1. A method for processing a digital mammographic image comprising:
    obtaining, on a processor-based system, a first mammographic image of an object; and
    processing, on the processor-based system, the first mammographic image;
wherein the step of processing the first mammographic image comprises:
    removing a brightness decline along an edge of the imaged object;
    optimizing contrast of the imaged object; and
    improving visualization of fine details within the imaged object;
wherein removing the brightness decline includes:
    performing in parallel a multi-scale decomposition of the first mammographic image into a low-pass portion, at least one band pass portion, and a high-pass portion, and subsequently modifying each portion independently, and then recombining the individual portions in a multi-scale reconstruction in order to output an optimized reconstructed mammographic image.

2. The method of claim 1, wherein the boundary regions along the breast edge of the at least one band pass portion and the high-pass portion are cut off and the cut off process is performed by multiplication of the at least one band pass portion and the high-pass portion with eroded masks derived from a mask containing the whole breast area.

3. The method of claim 1, wherein the low-pass portion is modified by subtracting pixel values of the pixels of the low-pass portion from a threshold value and setting the negative pixel values to zero.

4. A method for processing digital mammographic images comprising:
    obtaining, on an a processor-based system, a first mammographic image of an object, the first mammographic image including raw image data with pixel values assigned to each pixel, the first mammographic image also including a boundary region;
    balancing a brightness decline in the boundary region of the first mammographic image to produce a brightness-optimized mammographic image; and
    generating, on the processor-based system, a second mammographic image from the brightness-optimized mammographic image by optimizing the sharpness in the imaged object, wherein the sharpness in the imaged object is optimized in order to show fine details of the internal structures of the image object by, in parallel, dividing the brightness-optimized mammographic image through multi-scale decomposition into different non-overlapping portions, which are subsequently independently modified and recombined in a multi-scale reconstruction in order to output an optimized reconstructed mammographic image.

5. The method of claim 4, further comprising performing contrast adaption of the brightness-optimized mammographic image by dispersion of the pixel values of the brightness-optimized mammographic image.

6. The method of claim 4, wherein the brightness-optimized mammographic image is divided into a high-pass portion and a low-pass portion.

7. The method of claim 4, wherein contrast of the brightness-optimized mammographic image is optimized, by the pixel values of the brightness-optimized mammographic image by a gamma correction, so that after the gamma correction the average value of the pixel values corresponds to a pre-determined value within the imaged object of appropriate range.

8. The method of claim 4, wherein the different non-overlapping portions are submitted to a gamma correction in each portion for modification and reconstruction.

9. The method of claim 4, further comprising generating a skin line image from the first mammographic image and adding the skin line image to the second mammographic image.

10. The method of claim 9, wherein generation of the skin line image from the first mammographic image produces a gradient image where the boundary region of the imaged object is gradient-filtered.

11. The method of claim 9, wherein the skin line image forms an outline line of the imaged object produced for a mask that is extracted.

12. An apparatus configured for processing digital mammograms comprising:
   means for obtaining a first mammogram of an object, the first mammogram including a boundary region;
   means for reconciling a brightness decline in the boundary region of the first mammogram; and
   means for generating a brightness-optimized mammogram from different portions of a multi-scale decomposition of the first mammogram by independently modifying decomposed portions of the first mammogram in parallel and then recombining the portions in a multi-scale reconstruction in order to output an optimized reconstructed mammographic image.

* * * * *